United States Patent
Linford et al.

(10) Patent No.: US 9,126,227 B2
(45) Date of Patent: *Sep. 8, 2015

(54) THIN LAYER CHROMATOGRAPHY PLATES AND RELATED METHODS OF MANUFACTURE INCLUDING PRIMING PRIOR TO INFILTRATION WITH STATIONARY PHASE AND/OR PRECURSOR THEREOF

(71) Applicants: US SYNTHETIC CORPORATION, Orem, UT (US); BRIGHAM YOUNG UNIVERSITY, Provo, UT (US)

(72) Inventors: Matthew R. Linford, Orem, UT (US); David Scott Jensen, Provo, UT (US); Andrew E. Dadson, Provo, UT (US); Robert C. Davis, Provo, UT (US)

(73) Assignees: US SYNTHETIC CORPORATION, Orem, UT (US); BRIGHAM YOUNG UNIVERSITY, Provo, UT (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/186,996

(22) Filed: Feb. 21, 2014

(65) Prior Publication Data

US 2014/0170311 A1 Jun. 19, 2014

Related U.S. Application Data

(63) Continuation of application No. 13/368,869, filed on Feb. 8, 2012, now Pat. No. 8,702,984.

(51) Int. Cl.
*B05D 5/00* (2006.01)
*C23C 16/01* (2006.01)
(Continued)

(52) U.S. Cl.
CPC ............... *B05D 5/00* (2013.01); *B01J 20/324* (2013.01); *B01J 20/3204* (2013.01);
(Continued)

(58) Field of Classification Search
CPC ............... B01J 20/3297; B01J 20/3204; B01J 20/3223; B01J 20/3236; B01J 20/324; B01J 20/3259; B01J 20/3289; B05D 5/00; C23C 16/01; C23C 16/0272; C23C 16/402; C23C 16/403; C23C 16/45555; G01N 30/6095; G01N 30/92; B82Y 30/00
USPC ................. 210/658, 198.2; 73/61.54; 422/70; 436/162

See application file for complete search history.

(56) References Cited

U.S. PATENT DOCUMENTS

| 7,756,251 B2 | 7/2010 | Davis et al. |
| 2009/0086923 A1 | 4/2009 | Davis et al. |

(Continued)

FOREIGN PATENT DOCUMENTS

WO WO 2011/106694 9/2011

OTHER PUBLICATIONS

U.S. Appl. No. 13/368,869, Apr. 2, 2014, Issue Notification.
(Continued)

*Primary Examiner* — Ernest G Therkorn
(74) *Attorney, Agent, or Firm* — Dorsey & Whitney LLP

(57) ABSTRACT

In an embodiment, a method for manufacturing a thin layer chromatography ("TLC") plate is disclosed. The method includes forming a layer of elongated nanostructures (e.g., carbon nanotubes), priming the elongated nanostructures with one or more adhesion priming layers, and at least partially coating the elongated nanostructures with a coating. The coating includes a stationary phase and/or precursor of a stationary phase for use in chromatography. The stationary phase may be functionalized with hydroxyl groups by exposure to a base or acid. The stationary phase may further be treated with a silane (e.g., an amino silane) to improve the performance of the TLC plate. Embodiments for TLC plates and related methods are also disclosed.

25 Claims, 14 Drawing Sheets

(51) Int. Cl.
| | |
|---|---|
| *C23C 16/02* | (2006.01) |
| *C23C 16/40* | (2006.01) |
| *C23C 16/455* | (2006.01) |
| *B01J 20/32* | (2006.01) |
| *G01N 30/60* | (2006.01) |
| *G01N 30/92* | (2006.01) |
| *B82Y 30/00* | (2011.01) |

(52) U.S. Cl.
CPC ......... *B01J 20/3223* (2013.01); *B01J 20/3236* (2013.01); *B01J 20/3259* (2013.01); *B01J 20/3289* (2013.01); *B01J 20/3297* (2013.01); *C23C 16/01* (2013.01); *C23C 16/0272* (2013.01); *C23C 16/402* (2013.01); *C23C 16/403* (2013.01); *C23C 16/45555* (2013.01); *G01N 30/6095* (2013.01); *G01N 30/92* (2013.01); *B82Y 30/00* (2013.01)

(56) References Cited

U.S. PATENT DOCUMENTS

| | | |
|---|---|---|
| 2010/0285271 A1 | 11/2010 | Davis et al. |
| 2011/0000852 A1 | 1/2011 | Linford et al. |
| 2011/0089096 A1 | 4/2011 | Linford et al. |
| 2011/0192779 A1 | 8/2011 | Linford et al. |
| 2013/0199982 A1 | 8/2013 | Linford et al. |
| 2013/0224377 A1 | 8/2013 | Jensen |

OTHER PUBLICATIONS

U.S. Appl. No. 60/995,881, filed Sep. 28, 2007, Davis et al.
International Search Report and Written Opinion from International Application No. PCT/US2013/027609 mailed Apr. 17, 2013.
Jensen et al.; "Fabrication and Chemical Separation on Binder-Fee Carbon Nanotube TemplateThin Layer Chromatography Plates"; Pittcon Conference 2012, Feb. 27, 2013; retrived on Apr. 9, 2013; 1 page; http://ca.pittcon.org/technical+program.
Jensen et al.; "Stable, microfabricated thin layer chromatography plates without volume distortion on patterned, carbon and A1203-primed carbon nanotube forests", Journal of Chromatography A, vol. 1257, Aug. 4, 2012, pp. 195-203.
Kanyal et al.; "Effect of Catalyst Thickness on Carbon Nanotube (CNT) Morphology in CNT-Templated Fabrication of Thin Layer Chromatography Plates" Pittcon Conference 2012, Feb. 27, 2012; retrived on Apr. 9, 2009; 1 page; http://ca.pittcon.org/technical+program/tpabstra12.nsf/archiveframe.
Song, J.; Jensen, D. S.; Hutchison, D. N.; Turner, B.; Wood, T.; Dadson, A.; Vail, M. A.; Linford, M. R.; Vanfleet, R. R.; Davis, R. C., Adv. Funct. Mater. 2011, 21 (6), 1132-1139.
Hutchison, D. N.; Morrill, N. B.; Aten, Q.; Turner, B. W.; Jensen, B. D.; Howell, L. L.; Vanfleet, R. R.; Davis, R. C., J. Microelectromech. Syst 2010, 19 (1), 75-82.
Moulton, K.; Nicholas, B.; Morrill, N. B.; Konneker, A. M.; Jensen, B. D.; Vanfleet, R. R.; Allred, D. D.; Davis, R. C., J. Micromech. Microeng. 2011, Submitted for Review.
Billen, J.; Desmet, G., J. Chromatogr. A 2007, 1168 (1-2), 73-99.
John H, K., J. Chromatogr. A 1999, 831 (1), 3-15.
Reich, E.; Schibli, A., High-performance thin-layer chromatography for the analysis of medicinal plants. Thieme Medical Publishers, Inc.: New York, 2007. Front and back cover plus two copyright pages.
Van Le, T.; Ross, E. E.; Velarde, T. R. C.; Legg, M. A.; Wirth, M. J., Langmuir 2007, 23 (16), 8554-8559.
Bergna, H. E., Colloid Chemistry of Silica: An Overview. In Colloidal Silica Fundamentals and Applications, Bergna, H. E.; Roberts, W. O., Eds. Taylor & Francis Group: Boca Raton, 2006; vol. 131, pp. 9-35.
Gong, Q.-m.; Li, Z.; Li, D.; Bai, X.-d.; Liang, J., Solid State Commun. 2004, 131 (6), 399-404.
Gong, Q.-m.; Li, Z.; Bai, X.-d.; Li, D.; Liang, J., Compos. Sci. Tochnol. 2005, 65 (7-8), 1112-1119.
Kleckley, S.; Chai, G. Y.; Zhou, D.; Vanfleet, R.; Chow, L., Carbon 2003, 41 (4), 833-836.
Dillon, A. C.; Ott, A. W.; Way, J. D.; George, S. M., Surf. Sci. 1995, 322 (1-3), 230-242.
Ott, A. W.; Klaus, J. W.; Johnson, J. M.; George, S. M., Thin Solid Films 1997, 292 (1-2), 135-144.
Cavanagh, A. S.; Wilson, C. A.; Weimer, A. W.; George, S. M., Nanotechnol. 2009, 20 (25), 255602.
Hausmann, D.; Becker, J.; Wang, S.; Gordon, R. G., Science 2002, 298 (5592), 402-406.
Tleugabulova, D.; Zhang, Z.; Chen, Y.; Brook, M. A.; Brennan, J. D., Langmuir 2003, 20 (3), 848-854.
Herrmann, C. F.; Fabreguette, F. H.; Finch, D. S.; Geiss, R.; George, S. M., Appl. Phys. Lett. 2005, 87 (12), 2053358-2053360.
Farmer, D. B.; Gordon, R. G., Electrochem. Solid-State Lett. 2005, 8 (4), G89-G91.
Farmer, D. B.; Gordon, R. G., Nano Lett. 2006, 6 (4), 699-703.
Stevenson, R., Chapter 12 Instrumentation. In Journal of Chromatography Library, Heftmann, E., Ed. Elsevier: 2004; vol. vol. 69, pp. 469-518.
Hauck, H.; Bund, O.; Fischer, W.; Schulz, M., J. Planar Chromatogr.—Mod. TLC 2001, 14 (4), 234-236.
Hauck, H.; Schulz, M., Chromatographia 2003, 57 (0), S313-S315.
Bezuidenhout, L. W.; Brett, M. J., J. Chromatogr., A 2008, 1183 (1-2), 179-185.
Clark, J. E.; Olesik, S. V., Anal. Chem. 2009, 81 (10), 4121-4129.
Zewe, J. W.; Steach, J. K.; Olesik, S. V., Anal. Chem. 2010, 82 (12), 5341-5348.
Bakry, R.; Bonn, G. K.; Mair, D.; Svec, F., Anal. Chem. 2006, 79 (2), 486-493.
Han, Y.; Levkin, P.; Abarientos, I.; Liu, H.; Svec, F.; Fréchet, J. M. J., Anal. Chem. 2010, 82 (6), 2520-2528.
Sneh, O.; Wise, M. L.; Ott, A. W.; Okada, L. A.; George, S. M., Surf. Sci. 1995, 334 (1-3), 135-152.
Li, X.; Ci, L.; Kar, S.; Soldano, C.; Kilpatrick, S. J.; Ajayan, P. M., Carbon 2007, 45 (4), 847-851.
Kohler, J.; Kirkland, J. J., J. Chromatogr. 1987, 385, 125-150.
Kirkland, J. J.; Dilks Jr, C. H.; DeStefano, J. J., J. Chromatogr. A 1993, 635 (1), 19-30.
Stella, C.; Rudaz, S.; Veuthey, J.; Tchapla, A., Chromatographia 2001, 53 (0), S113-S131.
Park, J.; Ryu, Y.; Lim, H.; Lee, H.; Lee, Y.; Jang, M.; Suh, J.; Carr, P., Chromatographia 1999, 49 (11), 635-642.
Hill, D. W.; Kind, A. J., J. Lid. Chromatogr. 1993, 16 (18), 3941-3964.
Dolan, J. W., LCGC Eur. Sep. 2-4, 2003.
Asenath Smith, E.; Chen, W., Langmuir 2008, 24 (21), 12405-12409.
Zeng, X.; Xu, G.; Gao, Y.; An, Y., J. Phys. Chem. B. 2010, 115 (3), 450-454.
Zhang, F.; Sautter, K.; Larsen, A. M.; Findley, D. A.; Davis, R. C.; Samha, H.; Linford, M. R., Langmuir 2010, 26 (18), 14648-14654.
Mattevi, C.; Wirth, C. T.; Hofmann, S.; Blume, R.; Cantoro, M.; Ducati, C.; Cepek, C.; Knop-Gericke, A.; Milne, S.; Castellarin-Cudia, C.; Dolafi, S.; Goldoni, A.; Schloegl, R.; Robertson, J., J. Phys. Chem. C 2008, 112 (32), 12207-12213.
Esconjauregui, S.; Fouquet, M.; Bayer, B. C.; Ducati, C.; Smajda, R.; Hofmann, S.; Robertson, J., ACS Nano 2010, 4 (12), 7431-7436.
Wako Pure Chemical Industries Ltd. NH2 Silica Gel 60F254 Plate-Wako. http://www.wako-chem.co.jp/english/labchem/pdf/NH2_TLC_Plate.pdf.
Poole, C. F.; Poole, S. K., Anal. Chem. 1989, 61 (22), 1257A-1269A.
U.S. Appl. No. 13/368,869, Oct. 4, 2013, Office Action.
U.S. Appl. No. 13/368,869, Nov. 22, 2013, Notice of Allowance.
U.S. Appl. No. 61/634,358, filed Feb. 28, 2012, Jensen.
U.S. Appl. No. 13/368,869, Feb. 25, 2014, Interview Summary.
U.S. Appl. No. 13/773,969, Sep. 2, 2014, Office Action.
U.S. Appl. No. 13/773,969, Jan. 27, 2015, Office Action.
U.S. Appl. No. 13/773,969, Apr. 7, 2015, Office Action.

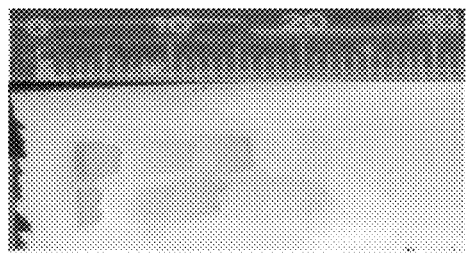 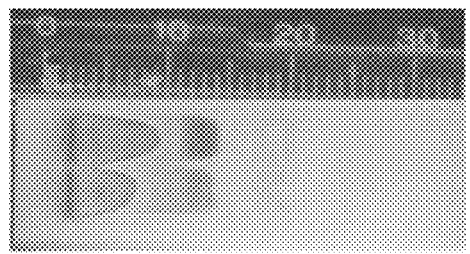
*Fig. 20A*  *Fig. 20B*
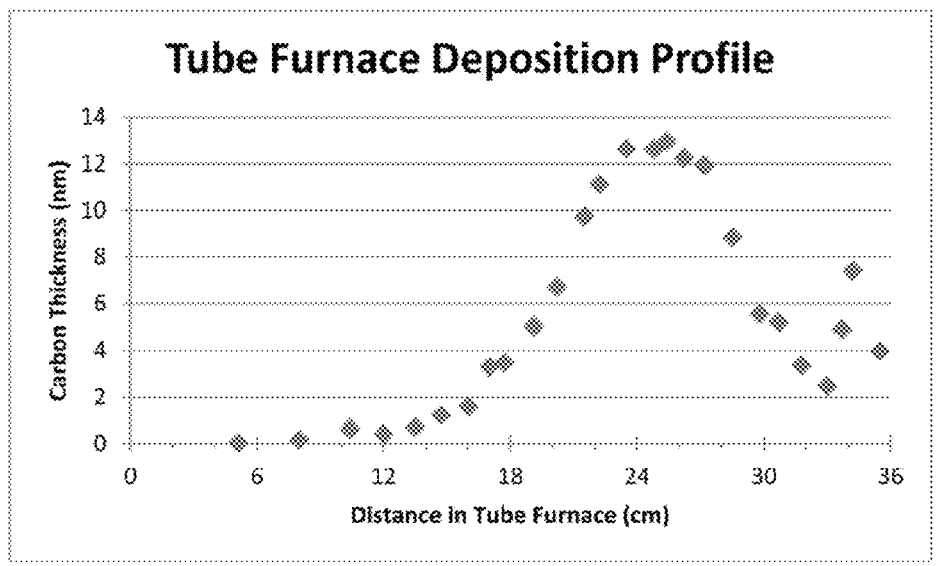
*Fig. 21*

THIN LAYER CHROMATOGRAPHY PLATES AND RELATED METHODS OF MANUFACTURE INCLUDING PRIMING PRIOR TO INFILTRATION WITH STATIONARY PHASE AND/OR PRECURSOR THEREOF

REFERENCE TO RELATED APPLICATIONS

This application is a continuation of Ser. No. 13/368,869 filed Feb. 8, 2013, now U.S. Pat. No. 8,702,984.

BACKGROUND

Chromatography and solid-phase extraction ("SPE") are commonly-used separation techniques employed in a variety of analytical chemistry and biochemistry environments. Chromatography and SPE are often used for separation, extraction, and analysis of various constituents, or fractions, of a sample of interest. Chromatography and SPE may also be used for the preparation, purification, concentration, and clean-up of samples.

Chromatography and SPE relate to any of a variety of techniques used to separate complex mixtures based on differential affinities of components of a sample carried by a mobile phase with which the sample flows, and a stationary phase through which the sample passes. Typically, chromatography and SPE involve the use of a stationary phase that includes an adsorbent packed into a cartridge, column, or disposed as a thin layer on a plate. Thin-layer chromatography ("TLC") employs a stationary phase that is spread in a thin layer on a carrier or substrate plate. A commonly-used stationary phase includes a silica-gel-based sorbent material.

Mobile phases are often solvent-based liquids, although gas chromatography typically employs a gaseous mobile phase. Liquid mobile phases may vary significantly in their compositions depending on various characteristics of the sample being analyzed and on the various components sought to be extracted and/or analyzed in the sample. For example, liquid mobile phases may vary significantly in pH and solvent properties. Additionally, liquid mobile phases may vary in their compositions depending on the characteristics of the stationary phase that is being employed. Often, several different mobile phases are employed during a given chromatography or SPE procedure. For example, gradient elution may be performed in which the mobile phase composition is varied with time.

A typical TLC plate is prepared by mixing an adsorbent (which acts as the stationary phase) with a small amount of an inert binder and water. The mixture may be spread as a relatively viscous slurry onto a carrier sheet. The resulting plate can then be dried and activated in an oven. The resulting stationary phase is bound in place to the carrier sheet or other substrate by the binder. The presence of the binder can lead to secondary interactions with the mobile phase, as well as a decrease in separation efficiency.

SUMMARY

Embodiments of the invention are directed to TLC plates, methods of using such TLC plates in chromatography, and related methods of manufacture in which a plurality of elongated stationary phase structures are formed and affixed to a substrate without the use of a separate binder. The elimination of the use of any binder may prevent unwanted secondary interactions, as well as improve separation efficiency.

In an embodiment, a method for manufacturing a TLC plate is disclosed. The method includes forming a catalyst layer over a substrate. A layer of elongated nanostructures (e.g., carbon nanotubes) is then formed over the catalyst layer. The elongated nanostructures so formed are then primed by at least partially coating the elongated nanostructures with one or more adhesion priming layers that promote subsequent deposition and adhesion of a coating that includes a stationary phase or precursor of a stationary phase for use in chromatography. The stationary phase coating or precursor thereof is then deposited on the one or more adhesion priming layers. The coating adheres to the one or more adhesion priming layers to a greater degree than the coating would adhere to the elongated nanostructures without the one or more adhesion priming layers. In some embodiments, after depositing the coating, the elongated nanostructures may be at least partially removed.

In an embodiment, a TLC plate is disclosed. The TLC plate includes a substrate, one or more residual priming adhesion layers disposed over the substrate that remain once elongate nanostructures have been at least partially removed, and a plurality of stationary phase structures that extend longitudinally away from the substrate. At least a portion of the plurality of stationary phase structures exhibits an elongated geometry and is substantially free of carbon nanotubes ("CNTs") used as templates for forming the stationary phase structures thereon. In an embodiment, the plurality of stationary phase structures is arranged on the substrate in a selected pattern. The stationary phase structure (e.g., a silica material) may further include a plurality of silanol groups bonded thereto which provide a functionalized surface for enhanced separation performance. Silane groups (e.g., an amino silane or an octadecyl silane) may also be bonded to the stationary phase structure surface for improved performance.

In an embodiment, a method of performing chromatography is disclosed. The method includes providing a TLC plate including a substrate, one or more residual priming adhesion layers disposed over the substrate that remain once elongate nanostructures (and any carbon adhesion priming layer(s)) have been oxidized away, and a plurality of stationary phase structures extending longitudinally away from the substrate. At least a portion of the plurality of stationary phase structures exhibits an elongated geometry. The method further includes applying a sample to be analyzed to the plurality of stationary phase structures of the TLC plate, and drawing a mobile phase through the plurality of stationary phase structures having the sample applied thereto. The different components of the sample may be separated as the mobile phase and the sample interact with the TLC plate.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

FIG. 10CC is a close-up transverse cross-sectional view of one of the primed CNTs of FIG. 10C.

FIG. 10DD is a close-up transverse cross-sectional view of one of the coated, primed, and coated CNTs of FIG. 10D.

FIG. 10EE is a close-up transverse cross-sectional view similar to FIG. 10DD, but once the CNTs have been burned off;

FIGS. 20A-20B show the separation results of a CAMAG test mixture on a TLC plate, with the TLC plates of FIGS. 20A and 20B having different geometries; and FIG. 21 shows the deposition profile for carbon in the employed tube furnace.

DETAILED DESCRIPTION

I. Introduction

Figure 1:
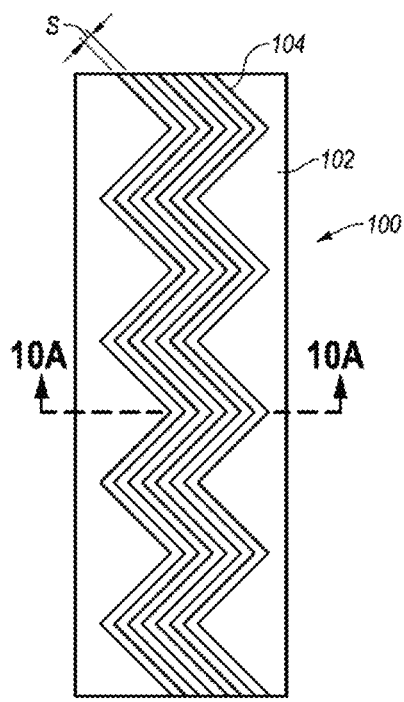
FIG. 1 is a schematic top plan view of an embodiment of a TLC plate intermediate structure including a substrate and a catalyst layer disposed over the substrate, with the catalyst layer exhibiting a zigzag pattern.

Embodiments of the invention are directed to TLC plates and related methods of manufacture and use. The disclosed TLC plates may include a plurality of elongated stationary phase structures affixed to a substrate without the use of a separate binder to provide a highly porous structure suitable for chromatography applications. The elimination of the use of any binder may prevent unwanted secondary interactions, as well as may improve separation efficiency.

The elongated stationary phase structures may be prepared with the use of one or more adhesion priming layers for promoting deposition and adhesion of the subsequently applied stationary phase materials or their precursor. Use of one or more priming layers aids in reducing or preventing any tendency of the elongated stationary phase structures to delaminate, buckle, or otherwise separate from the substrate to which they are attached. In other words, they exhibit greater mechanical stability. Use of an adhesion priming layer also aids in deposition of the stationary phase, allowing the deposition to occur more quickly and with greater stationary phase thickness for a given processing cycle.

II. Methods for Manufacturing TLC Plates and Resulting TLC Plates

In various embodiments, a TLC plate may be manufactured by forming a layer of elongated nanostructures on a substrate, priming the formed elongated nanostructures with one or more adhesion priming layers for promoting deposition and adhesion of a subsequent coating, and then at least partially coating the elongated nanostructures with a coating that comprises a stationary phase and/or a precursor to the stationary phase for use in chromatography. While the description hereinbelow uses CNTs as an example of a suitable elongated nanostructure, other elongated nanostructures may be used, such as semiconductor nanowires with or without a porous coating, metallic nanowires with or without a porous coating, nanopillars formed by nanoimprint lithography, combinations of the foregoing, or any other suitable nanostructure.

The CNTs may generally be vertically aligned relative to one another, although some contact and/or at least partially intertwining of adjacent CNTs may occur, which may provide increased mechanical stability to individual "hedge" portions of a given pattern, or to the overall CNT forest. The CNTs are primed with one or more adhesion priming layers, and may then be coated with a stationary phase that has a thickness less than the CNT hedge spacing (i.e., leaving a "flow channel"), which results in a porous medium through which separation by means of chromatography may occur. The resulting pattern may thus include a series of hedges separated by flow channels. The CNT forest is used as a framework on which the primer and then the stationary phase may be coated and/or formed, resulting in a finished structure that is generally free of any binder for binding the stationary phase to the substrate.

The substrate may include a base, a backing layer disposed on the base, and a catalyst layer disposed on the backing layer that is used to catalyze growth of CNTs over the substrate. Generally, the catalyst layer may be deposited onto the backing layer by any suitable technique. For example, placement of the catalyst layer may be accomplished using a photolithography process, such as masking the catalyst layer and etching to remove regions of the catalyst layer exposed through the mask. Such photolithography processes may be used to produce a catalyst layer having a selected non-linear (e.g., zigzag) pattern. Other patterning processes such as shadow masking with a stencil during catalyst deposition or printing may also be used. In another embodiment, the catalyst layer may be applied so as to coat substantially the entire substrate.

The catalyst layer may comprise any suitable material that catalyzes growth of CNTs under suitable growing conditions (e.g., heating and exposure to a process gas such as $H_2$ and a carbon containing gas such as $C_2H_4$). Various transition metals may be suitable for use as a catalyst layer. Suitable metals include, but are not limited to, iron, nickel, copper, cobalt, alloys of the forgoing metals, and combinations thereof.

The backing layer of the substrate provides support for the structures of the TLC plate. For example, the backing layer provides a support on which the catalyst layer may be deposited, and may also function as a diffusion barrier to help prevent a chemical reaction between the catalyst layer and the base. Examples of backing layer materials may include, but are not limited to, silica (e.g., fused silica), alumina, a low-expansion high-temperature borosilicate glass (e.g., Pyrex 7740 and/or Schott Borofloat glass), steel (e.g., stainless steel), a silicon wafer, a nickel substrate, or any other high-temperature glass or other suitable material. In embodiments where the backing layer comprises a material other than alumina, the backing layer may be prepared for CNT growth by application of a thin layer of alumina over the non-alumina backing layer. The alumina layer may have a thickness between about 5 nm and about 100 nm, more specifically between about 10 nm and about 50 nm, and most specifically between about 20 nm and about 40 nm (e.g., about 30 nm).

A catalyst layer (e.g., iron) may be applied over the backing layer. The catalyst layer may have a thickness between about 0.1 nm and about 15 nm, more particularly between about 0.5 nm and about 10 nm, and even more particularly between about 0.5 nm and about 8 nm (e.g., about 2 to about 7 nm). For example, the catalyst layer may have a thickness of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, or about 15 nm. Although specific catalyst layer thicknesses are disclosed above, the inventors have further found that varying the thickness of the catalyst layer affects some or each of the diameter, density, or height of CNTs grown under otherwise identical conditions. As such, according to an embodiment, the catalyst layer thickness may be altered to change one or more of diameter, density, or height of the grown CNTs.

Figure 2:
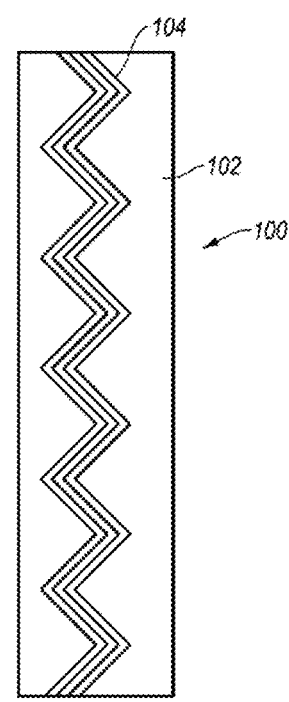
FIG. 2 is a schematic top plan view of another embodiment of a TLC plate intermediate structure similar to FIG. 1, but the catalyst layer exhibits an alternative zigzag pattern.
Figure 3:
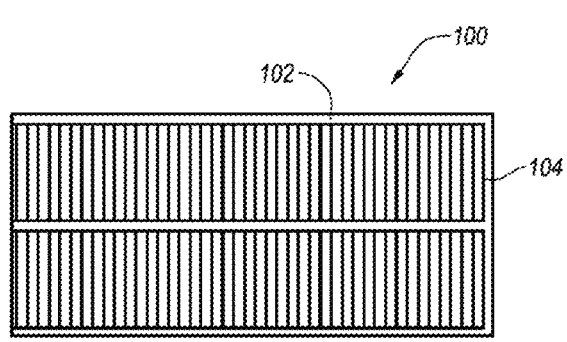
FIG. 3 is a schematic top plan view of another embodiment of a TLC plate intermediate structure similar to FIG. 1, but the catalyst layer exhibits a substantially parallel spacing pattern.
Figure 4:
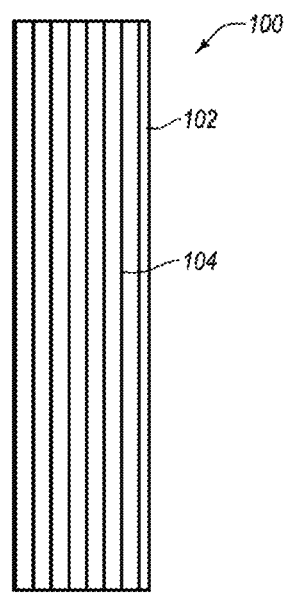
FIG. 4 is a schematic top plan view of another embodiment of a TLC plate intermediate structure similar to FIG. 3, but the catalyst layer exhibits another substantially parallel spacing pattern.
Figure 5:
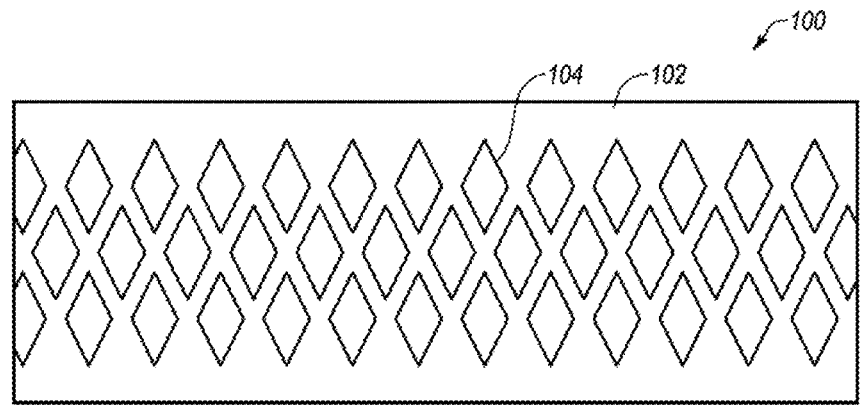
FIG. 5 is a schematic top plan view of another embodiment of a TLC plate intermediate structure similar to FIG. 1, but the catalyst layer exhibits a diamond-shaped pattern.
Figure 6:
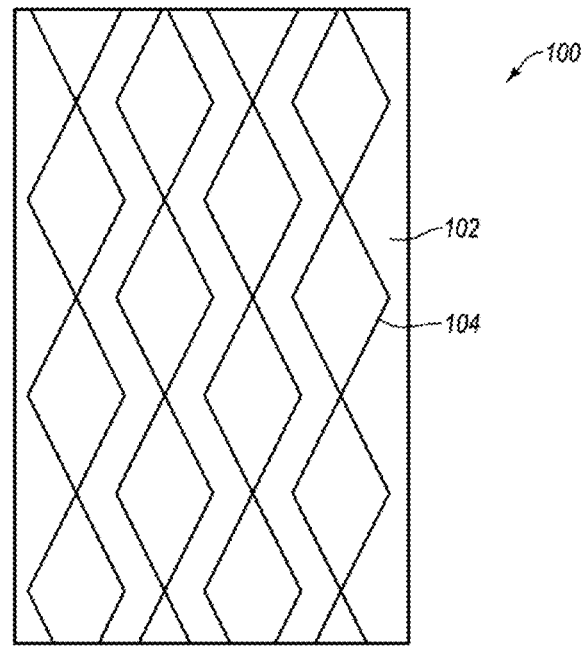
FIG. 6 is a schematic top plan view of another embodiment of a TLC plate intermediate structure similar to FIG. 5, but the catalyst layer exhibits another diamond-shaped pattern.
Figure 7:
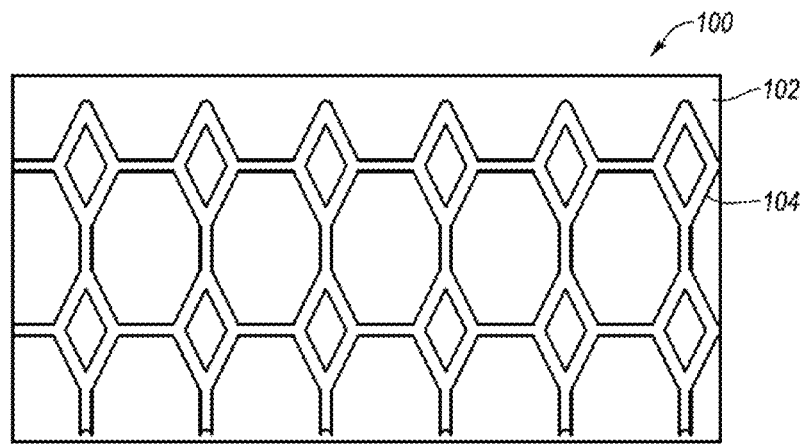
FIG. 7 is a schematic top plan view of another embodiment of a TLC plate intermediate structure similar to FIG. 1, but the catalyst layer exhibits a honeycomb-like pattern.
Figure 8:
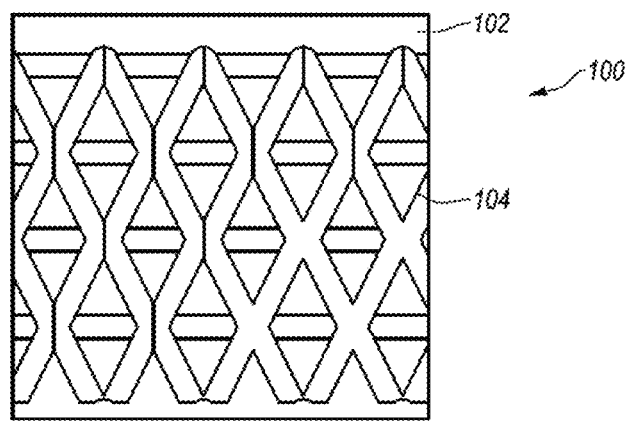
FIG. 8 is a schematic top plan view of another embodiment of a TLC plate intermediate structure similar to FIG. 7, but the catalyst layer exhibits another honeycomb-like pattern.
Figure 9:
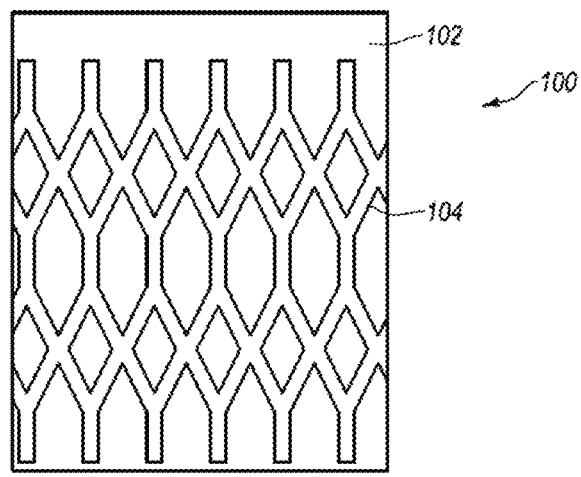
FIG. 9 is a schematic top plan view of another embodiment of a TLC plate intermediate structure similar to FIG. 7, but the catalyst layer exhibits another honeycomb-like pattern.
Figure 10A:
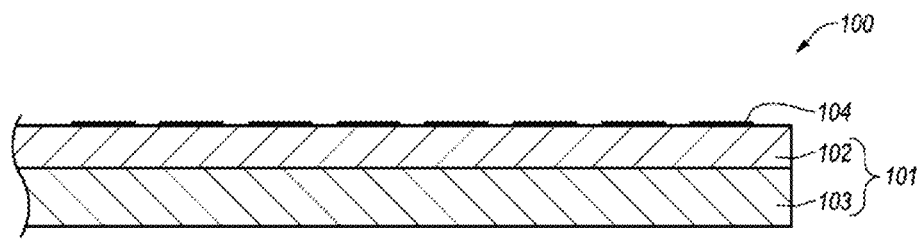
FIG. 10A is a cross-sectional view of the TLC plate intermediate structure of FIG. 1.

The catalyst layer may be applied in a selected linear pattern, a selected non-linear pattern, or other selected pattern, or may be applied over substantially an entire surface of the backing layer. Various embodiments of patterns for the catalyst layer are shown in FIGS. 1-9. For example, FIGS. 1 and 10A show a TLC plate intermediate structure 100 including a substrate 101 having a backing layer 102 disposed on a base 103 and a catalyst layer 104 formed on backing layer 102 in a non-linear zigzag pattern, with the patterned catalyst represented by the dark lines. In some embodiments, periodic breaks may be formed in some or all of the zigzag portions of catalyst layer 104 to provide a more uniform average mobile phase velocity to the TLC plate to be ultimately formed. FIG. 2 illustrates another embodiment of a zigzag pattern for catalyst layer 104, with the patterned catalyst represented by the dark lines (e.g., a series of "hedges" separated from one another by adjacent flow channels). FIGS. 3 and 4 each show a TLC plate intermediate structure 100 including substrate 101 having backing layer 102 disposed on base 103 and catalyst layer 104 formed on backing layer 102 in substantially parallel patterns according to another embodiment, with the patterned catalyst represented by the dark lines. FIGS. 5 and 6 each shows a TLC plate intermediate structure 100 including substrate 101 having backing layer 102 disposed on base 103 and catalyst layer 104 formed on backing layer 102 in various repeating diamond patterns according to various embodiments, with the diamonds representing the catalyst. FIGS. 7-9 each shows a TLC plate intermediate structure 100 including a substrate 101 having backing layer 102 disposed on base 103 and catalyst layer 104 formed on backing layer 102 in different honeycomb-like patterns according to various embodiments. FIGS. 1 and 2 and 5-9 each show a non-linear catalyst pattern, while the patterns of FIGS. 3 and 4 show generally linear catalyst patterns.

The catalyst layer 104 may be patterned to exhibit any desired spacing between adjacent portions of the patterned catalyst layer 104. For example, an average bed spacing "S" is shown in FIG. 1. In an embodiment, an average bed spacing between adjacent portions of patterned catalyst layer 104 is between about 0.2 μm and about 50 μm, more particularly between about 0.5 μm and about 20 μm, and most particularly between about 1 μm and about 10 μm (e.g., about 10 μm). One of ordinary skill in the art will appreciate that catalyst layer 104 may be formed so as to have any desired pattern and/or spacing "S." In another embodiment, the catalyst layer 104 may be formed so as to cover substantially the entire backing layer 102, lacking any particular distinct pattern. In some embodiments, catalyst layer 104 is spaced inwardly from edges of backing layer 102 in order to substantially prevent growth of CNTs on the edges. In some embodiments, the spacing "S" may vary in one or two directions, such as from zigzag portion to zigzag portion.

With catalyst layer 104 formed on backing layer 102, TLC plate intermediate structure 100 may be placed onto a suitable support (e.g., a quartz support) within a furnace and heated to a temperature within a range of about 600° C. to about 900° C., more particularly between about 650° C. to about 850° C., and even more particularly to between about 700° C. to about 800° C. (e.g., about 750° C.). Prior to CNT growth, the catalyst layer 104 may be annealed in an annealing process in which $H_2$ or another process gas is flowed over the catalyst layer 104 (e.g., within a fused silica tube) while the temperature is increased from ambient temperature to the temperature at which CNT growth will occur. Flow of $H_2$ may be about 300 $cm^3$/min or other suitable flow rate.

A process gas (e.g., $H_2$, ammonia, $N_2$, or combinations thereof) and a carbon-containing gas (e.g., acetylene, ethylene, ethanol, methane, or combinations thereof) are introduced and flowed over the catalyst layer 104. A noble gas (e.g., argon) may also be included with the carbon-containing gas stream to control the rate of growth of CNTs on and over the catalyst layer 104. Flow of the process gas and carbon-containing gas (e.g., ethylene) may be within a ratio of about 0.5:1 to about 1, more particularly between about 0.55:1 and about 0.85:1, and even more particularly between about 0.6:1 and about 0.8:1.

Once the desired height of CNT growth is achieved, flow of the process gas and carbon-containing gas are turned off, and the furnace chamber may be purged with flow of a noble gas (e.g., argon) as the furnace is partially cooled, for example to a temperature between about 100° C. to about 300° C., more particularly between about 150° C. to about 250° C., and even more particularly to between about 175° C. to about 225° C. (e.g., about 200° C.).

In one embodiment, and in order to achieve a higher aspect ratio of base width to CNT height, a "start/stop" method may be employed. For example, the carbon-containing gas may be turned off during CNT growth, causing the CNTs to grow in a myriad of directions. This type of growth may be desired in some embodiments, as it may lead to more mechanically stable CNTs (e.g., such adjacent CNTs may be more likely to contact and/or at least partially intertwine with one another).

Figure 10B:
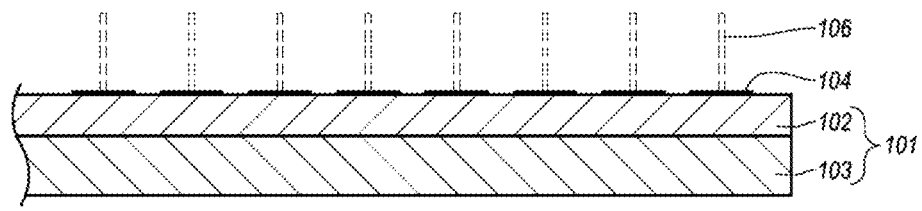
FIG. 10B is a cross-sectional view of the TLC plate intermediate structure of FIG. 10A with CNTs grown on the catalyst layer.

FIG. 10B is a cross-sectional view of an embodiment of a structure similar to that of FIGS. 1 and 10A in which CNTs 106 have been grown on and over catalyst layer 104. CNTs 106 may be grown to extend longitudinally away from the substrate 101. For example, the CNTs may extend substantially perpendicular (i.e., vertical) to respective surfaces of catalyst layer 104 and substrate 101. Grown CNTs 106 may be single walled or multi-walled, as desired. Grown CNTs 106 may have an average diameter between about 3 nm and about 20 nm, more particularly between about 5 nm and about 10 nm (e.g., about 8.5 nm) and an average length of about 1 μm to about 2000 μm, about 5 μm to about 1000 μm, about 10 μm to about 500 μm, about 20 μm to about 400 μm, about 20 μm to about 200 μm, about 100 μm to about 300 μm, about 10 μm to about 100 μm, or about 20 μm to about 200 μm. The grown CNTs 106 may exhibit an average aspect ratio (i.e., ratio of average length to average diameter) of about 10,000 to about 2,000,000, such about 10,000 to about 1,000,000, or about 100,000 to about 750,000.

The average length to which CNTs 106 are grown may be chosen based on the particular chromatography application. For example, the average length of the CNTs 106 may be about 2 μm to about 100 μm for ultra-thin layer chromatography ("UTLC"), the average length of the CNTs 106 may be about 100 μm to about 300 μm for high-performance thin layer chromatography ("HPTLC"), and the average length of the CNTs 106 may be about 500 μm to about 2000 μm for preparative liquid chromatography ("PLC").

Additional details regarding growth of CNTs 106 may be found in U.S. patent application Ser. Nos. 12/239,281 and 12/239,339 entitled X-RAY RADIATION WINDOW WITH CARBON NANOTUBE FRAME. Both of the above applications claim priority to U.S. Provisional Patent Application No. 60/995,881. U.S. patent application Ser. No. 12/239,281 and Ser. No. 12/239,339 and U.S. Provisional Patent Application No. 60/995,881 is each incorporated herein, in its entirety, by this reference. Further details may be found in U.S. patent application Ser. No. 13/035,645 filed Feb. 25, 2011, also herein incorporated by reference in its entirety.

Although CNTs 106 are illustrated as being uniformly spaced, CNTs 106 may be at least partially intertwined with each other to form a vertical wall of CNTs 106. Furthermore, adjacent "hedges" of CNTs 106 may comprise a plurality of grouped CNTs, which may be at least partially intertwined with each other (e.g., more than one CNT may be grown side by side with the illustrated CNT on the shown catalyst layer 104). Only one CNT is shown on each catalyst layer 104 for simplicity. Such hedges of CNTs may be separated by a flow channel between another adjacent hedge. As previously discussed, the at least partial intertwining and/or contact of CNTs 106 with each other helps reduce, limit, or prevent the vertical wall of CNTs 106 from bending out of plane. Furthermore, the rigidity of the wall of CNTs 106 may be further enhanced to reduce, limit, or prevent out of plane bending thereof by patterning catalyst layer 104 in a selected non-linear pattern (e.g., the pattern shown in FIG. 1) and growing respective portions of CNTs 106 on the individual non-linear portions of catalyst layer 104 to form respective walls of CNTs 106.

The CNTs are used as a framework to be infiltrated with a material that may increase the mechanical stability of the overall structure and provide a stationary phase for use in chromatography applications. That said, it has been found that application of one or more priming layers to the CNTs in preparation for infiltration also further increases the mechanical stability of the overall structure. For example, application of the priming layer(s) contributes to prevention or minimization any tendency of the resulting stationary phase to delaminate, buckle, or otherwise separate from the substrate 101.

Figure 10C:
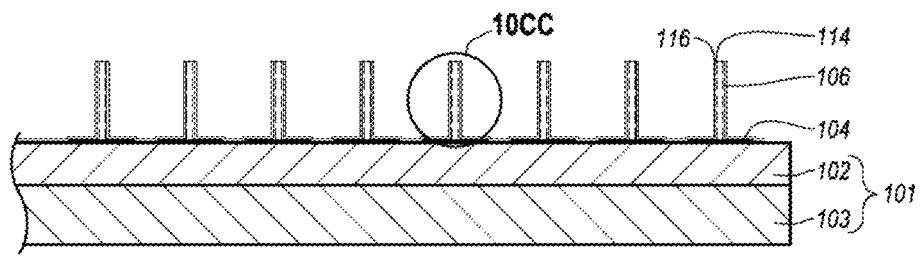
FIG. 10C is a cross-sectional view of the TLC plate intermediate structure of FIG. 10B once the CNTs have been primed with two adhesion priming layers.
Figure 10C:
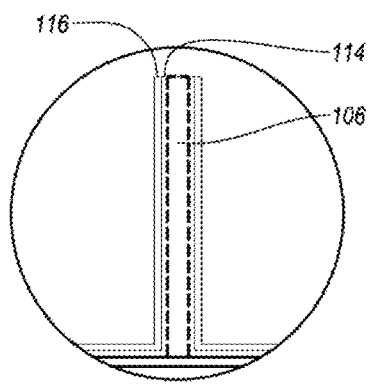

Referring to FIG. 10C, after growth, CNTs 106 may be coated with one or more adhesion priming layers for promoting subsequent deposition of a later applied coating that includes a stationary phase or precursor of a stationary phase for use in chromatography. The one or more adhesion priming layers may partially or substantially completely coat CNTs 106 and intervening regions over backing layer 102 of substrate 101 between adjacent CNTs 106 and/or groups of CNTs 106. FIG. 10CC shows application of two priming layers 114 and 116. Each priming layer 114, 116 may be relatively thin. For example, the thickness of any given priming layer may be from about 1 nm to about 20 nm, from about 2 nm to about 15 nm, or from about 2 nm to about 12 nm. The priming layer may thus be significantly thinner than a subsequently applied stationary phase or precursor thereof (which may typically be about 100 nm in thickness). One purpose of the priming layer is to promote mechanical stability, subsequent deposition, and adhesion of the subsequently deposited stationary phase or precursor thereof.

Materials used for priming may be the same or similar materials as those used for infiltration with the stationary phase or its precursor. Examples of such priming materials include, but are not limited to, elemental silicon, silicon dioxide, silicon nitride, elemental aluminum, aluminum oxide, elemental zirconium, zirconium oxide (e.g., zirconium dioxide), elemental titanium, titanium oxide, amorphous carbon, graphitic carbon, and combinations of the foregoing. In one embodiment, the priming layers are selected from amorphous carbon, aluminum oxide, and combinations thereof. For example, in an embodiment, priming layer 114 adjacent to CNTs 106 may comprise amorphous carbon, while priming layer 116 adjacent to priming layer 114 may comprise alumina (i.e., aluminum oxide).

Figure 14A:
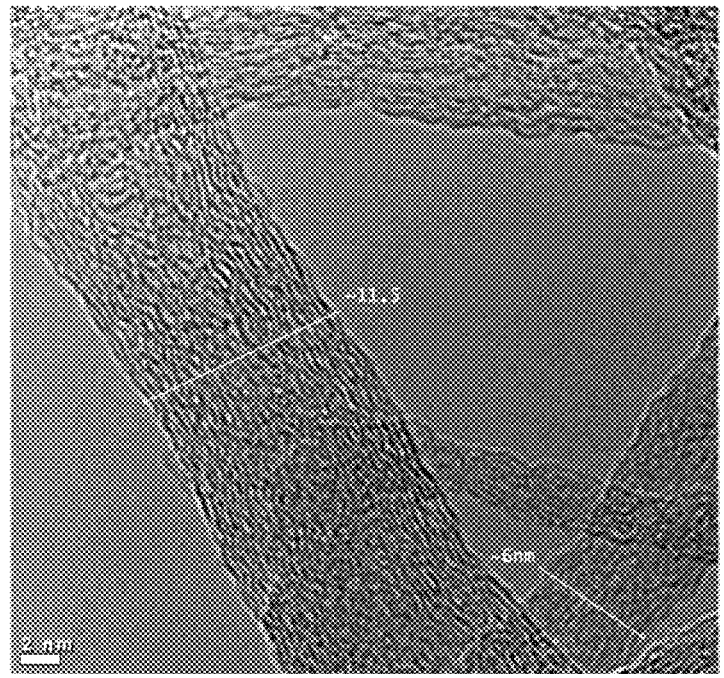
FIG. 14A shows a transmission electron microscopy ("TEM") image of CNTs as grown.
Figure 14B:
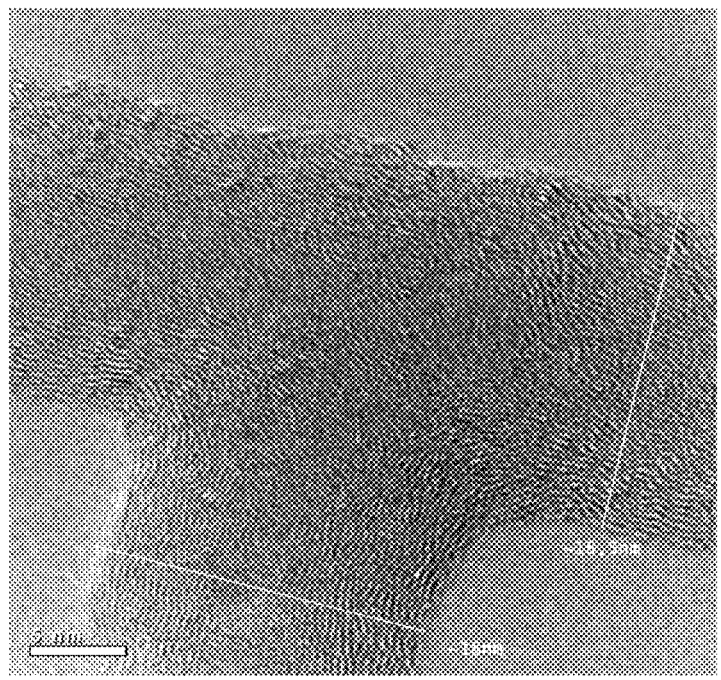
FIG. 14B shows a TEM image of CNTs after having been primed with amorphous carbon.

Application of the one or more priming layers may be achieved at appropriate temperatures. For example, deposition of amorphous carbon can be carried out at a temperature at a somewhat higher range than that described above relative to CNT growth. For example, deposition of amorphous carbon can be carried out from about 800° C. to about 1000° C., from about 850° C. to about 950° C., or about 900° C. while flowing ethylene and argon over the CNTs. In one embodiment, the amorphous carbon priming layer is formed to be not more than about 10 nm thick, from about 2 nm to about 8 nm thick, or from about 3 nm to about 5 nm thick. FIGS. 14A-14B illustrate TEM images of CNTs prior to priming (see FIG. 14A) and after priming with a layer of amorphous carbon (see FIG. 14B).

Deposition of alumina as a priming layer by ALD may be carried out at significantly lower temperatures, e.g., from about 150° C. to about 350° C., from about 200° C. to about 300° C., or about 250° C. while cycling trimethylaluminum and water in a serial, repeating (e.g., in an ABAB fashion) for a desired number of cycles. Deposition of about 0.1 nm per cycle is typical. In one embodiment, the alumina layer is formed to be from about 5 nm to about 15 nm thick, or from about 6 nm to about 12 nm thick.

In one embodiment, at least one of the priming layers may be a material that is different from the subsequently applied stationary phase or precursor thereof (e.g., not silicon or silicon dioxide where the stationary phase is such a material). In one embodiment, all priming layers may be different from the subsequently applied stationary phase or precursor thereof. Furthermore, where more than one priming layer is applied, the priming layers may comprise different materials. Deposition of the one or more priming layers may be accomplished through atomic layer deposition ("ALD"), ALD-like processes (also referred to herein as pseudo ALD) or another suitable process, or from a solution via solution deposition processing. It has surprisingly been found that application of one or more relatively thin priming layers (e.g., a few nanometers) may advantageously result in significantly less incidence of delamination of the subsequently applied stationary phase or precursor thereof from the substrate. It also has been found to promote better adhesion and growth of the stationary phase during infiltration (i.e., resulting in faster fabrication).

Figure 10D:
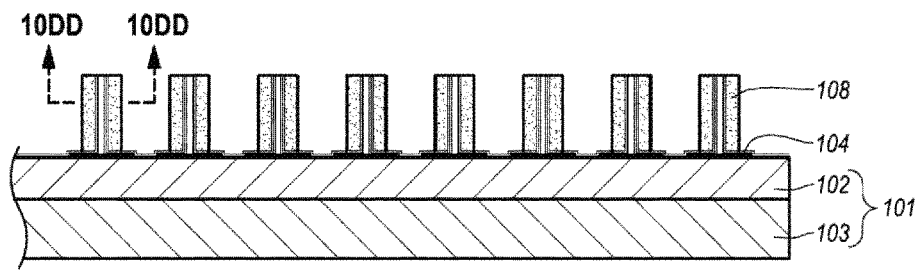
FIG. 10D is a cross-sectional view of the TLC plate intermediate structure of FIG. 10C once the primed CNTs have been at least partially coated by a stationary phase coating.
Figure 10D:
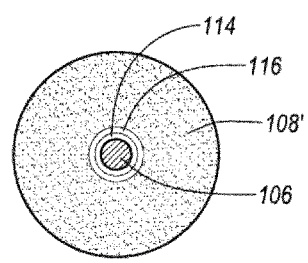

Once CNTs 106 have been primed, they may be infiltrated with a stationary phase or stationary phase precursor. Referring to FIG. 10D, after growth, primed CNTs 106 may be infiltrated with one or more infiltrants (e.g. a precursor gas) so that a coating 108 deposits on priming layer 116 adjacent the CNTs 106. Coating 108 comprises a stationary phase and/or a precursor to the stationary phase. Examples of materials for coating 108 include, but are not limited to, elemental silicon (e.g., deposited from a precursor $SiH_4$ gas), silicon dioxide, silicon nitride, elemental aluminum, aluminum oxide, elemental zirconium, zirconium oxide (e.g., zirconium dioxide), elemental titanium, titanium oxide, amorphous carbon, graphitic carbon, and combinations of the foregoing. Because the choice of coating 108 may change the selectivity of the resulting TLC plate, coating 108 used for manufacture of any given TLC plate may be selected depending on the intended use of the TLC plate.

In one embodiment, infiltration of CNTs 106 may be accomplished using chemical vapor deposition (e.g., low pressure chemical vapor deposition ("LPCVD")) or another suitable deposition process (e.g., ALD or pseudo-ALD). Silica may be directly deposited by cycling trimethylaluminum ("TMA") and tris(tert-butoxy)silanol $(((CH_3)_3O)_3SiOH)$ ("TTBS") in a serial, repeating (e.g., in an ABAB fashion) fashion. For example, where depositing silica, the TLC plate intermediate structure shown in FIG. 10B may be placed into a furnace and heated to about 150° C. to about 350° C., more particularly between about 200° C. to about 300° C., and even more particularly to between about 225° C. to about 250° C. (e.g., about 235° C.). Under such conditions, the TMA/TTBS reactants flow over primed CNTs 106 to cause a coating 108 (see FIG. 10D) of silica to form on primed CNTs 106. A thickness of about 13 nm per cycle can be achieved, for a final silica thickness of about 50 to about 125 nm (e.g., about 100 nm) after a desired number of cycles (e.g., 8 cycles).

Figure 13A:
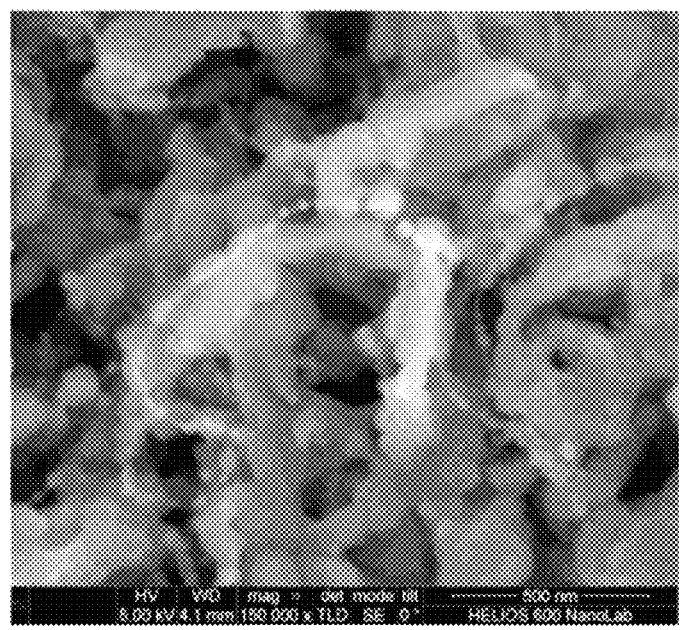
FIG. 13A shows an SEM image of a TLC stationary phase formed by directly applying a silica stationary phase over CNTs through pseudo atomic layer deposition ("ALD"), without any priming layer between the CNTs and the silica stationary phase.
Figure 13B:
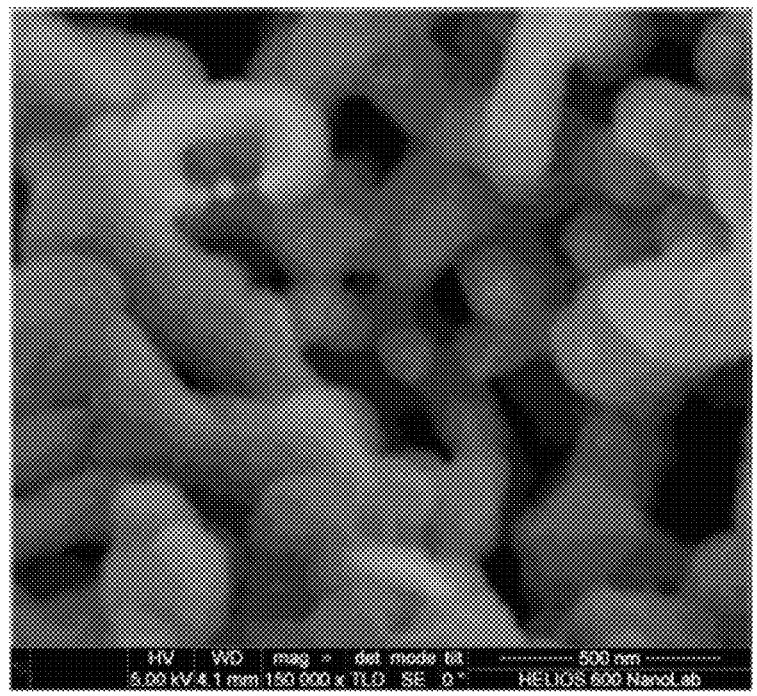
FIG. 13B shows an SEM image of a TLC stationary phase formed by applying a silica stationary phase over CNTs through pseudo atomic layer deposition ("ALD"), where the CNTs were first primed with amorphous carbon.
Figure 13C:
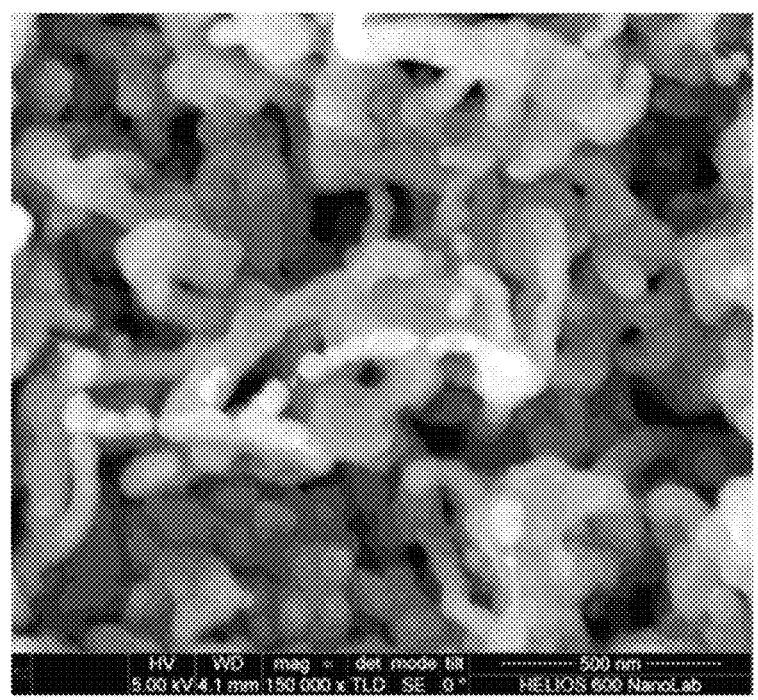
FIG. 13C shows an SEM image of a TLC stationary phase formed by applying a silica stationary phase over CNTs through pseudo atomic layer deposition ("ALD"), where the CNTs were first primed with alumina.
Figure 13D:
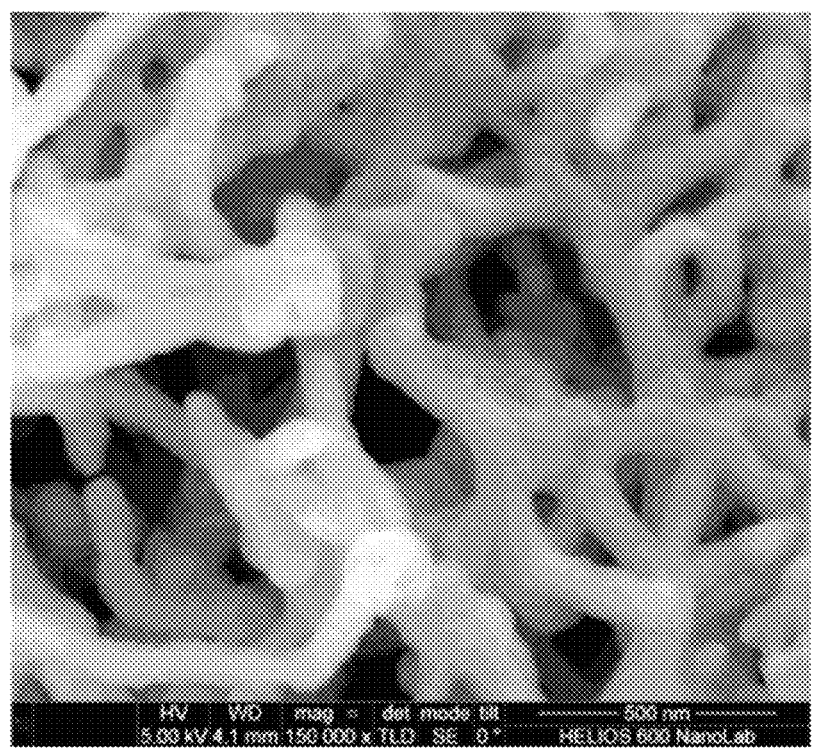
FIG. 13D shows an SEM image of a TLC stationary phase formed by applying a silica stationary phase over CNTs through pseudo atomic layer deposition ("ALD"), where the CNTs were first primed with a priming layer of amorphous carbon followed by a priming layer of alumina.

FIG. 13A shows an SEM micrograph of a CNT structure that was infiltrated with 8 cycles of a silicon dioxide coating (about 104 nm thick). No priming of the CNTs was employed in FIG. 13A. FIG. 13B shows an SEM micrograph of a CNT structure that was first primed with a 4 nm layer of amorphous carbon and then infiltrated with 8 cycles of a silicon dioxide coating (about 104 nm thick). FIG. 13C shows an SEM micrograph of a CNT structure that was first primed with a 7 nm layer of alumina, and then infiltrated with 8 cycles of a silicon dioxide coating (about 104 nm thick). FIG. 13D shows an SEM micrograph of a CNT structure that was first primed with a 4 nm layer of amorphous carbon, followed by priming with a 7 nm layer of alumina, and then infiltrated with 8 cycles of a silicon dioxide coating (about 104 nm thick).

When depositing silicon (which is later oxidized to silica), the TLC plate intermediate structure shown in FIG. 10B may be placed into a furnace and heated to about 500° C. to about 650° C., more particularly between about 540° C. to about 620° C., and even more particularly to between about 560° C. to about 600° C. (e.g., about 580° C.). During infiltration, the infiltration pressure may be maintained at less than about 400 mTorr. For example, the infiltration pressure may be maintained between about 50 mTorr and about 400 mTorr, more particularly between about 100 mTorr to about 300 mTorr, and even more particularly to between about 150 mTorr to about 250 mTorr (e.g., about 200 mTorr). The amount of deposition of the coating material achieved may be affected by process time. For example, process time for silicon infiltration may be between about 0.5 hours and about 10 hours, more particularly between about 1 hours and about 5 hours, and most particularly between about 1 hours and about 4 hours (e.g., about 3 hours).

Amorphous carbon infiltration of the CNTs 106 may be performed using a carbon source flowing through the fused silica tube at elevated temperatures. For example, ethylene may be flowed, for example, at a rate of 170 $cm^3$/min mixed with argon at a flow rate of 200 $cm^3$/min and at a temperature of about 900° C. Due to the light absorptive characteristics of amorphous carbon, the detection of analytes after separation may require a post sample preparation. This process may include marking the analytes with an oxidation stable marker and removing the carbon in a high temperature oxygen environment (e.g., with an oxygen plasma). For example, the developing agent may comprise silane, either in the gas phase or in solution, which would be applied to the TLC plate. In an oxidative environment (e.g., an oven, a plasma, or flame), the carbon would be burned away leaving a pattern of $SiO_2$ that would reveal where migration of analytes had occurred.

CNTs 106 may be infiltrated with elemental silicon by LPCVD and then oxidized, if needed or desired, to form $SiO_2$. Other deposition processes for $SiO_2$ include direct $SiO_2$ LPCVD, ALD, or by other CVD processes with $SiH_4$ and $O_2$ or $SiH_2Cl_2$ with $N_2O$, or by other methods for CNT infiltration that will be apparent to one of skill in the art in light of the present disclosure. The inventors have performed pseudo-ALD of silica directly onto the primed CNTs. The inventors have also performed LPCVD infiltration of CNTs with elemental silicon followed by dry oxidation. The silicon infiltration process employed $SiH_4$ as the source for elemental silicon. The silicon infiltration was done by flowing $SiH_4$ at a rate of about 20 $cm^3$/min at a temperature of about 530° C. with a pressure of about 160 mTorr for about 1-3 hours, depending on film thickness (degree of infiltration) desired.

After the silicon deposition, the material is placed into a furnace in air and treated to between about 500° C. and about 1000° C. (e.g., about 850° or 900° C.) for between about 1 and about 10 hours. This process converted the elemental silicon to silicon dioxide, while also removing CNTs 106 by oxidizing them into CO and/or $CO_2$ thereby leaving elongated stationary phase structures made from silicon dioxide without any significant amount of CNTs 106 filling. However, in additional embodiments, the CNTs 106 may not be removed or they may only be partially removed. Direct deposition of silica may be advantageous for one or more reasons, one of which is that the oxidizing step for removal of CNTs can be achieved at lower temperature (e.g., not more than 650° C., from about 500° C. to about 650° C., or about 600° C.) than where oxidation of the stationary phase precursor is also required. Depending on the extent of the oxidation process, the elongated stationary phase structures may be substantially solid nanowires without a hollow central portion where the CNTs 106 where present. This process produces a white and/or transparent $SiO_2$ material that may be used for chromatography. Silicon infiltration between and around the CNT wires may be nearly complete (e.g., at least about 90%).

ALD processes may be used to infiltrate CNTs 106 with a coating (e.g., a conformal coating) of a selected material having chromatographic abilities, or which may be subsequently processed to result in such abilities. The above-described pseudo-ALD process enables deposition of a relatively very thick layer of silica in a single cycle (e.g., about 13 nm per cycle). Other similar processes may alternatively be used. For example, ALD may be used to infiltrate CNTs with $SiO_2$. One such process may use $SiCl_4$ and water at a selected temperature. $SiCl_4$ is introduced into the chamber containing CNTs 106 and is allowed to react therewith for a predetermined time. After finishing the self-limiting chemisorptions/physisorption process, which may include removing most of the silicon precursor ($SiCl_4$), water is introduced into the chamber which reacts with the bound $SiCl_4$ to produce a conforming layer of $SiO_2$ on CNTs 106. Most, or all, of the water in the chamber may then be removed. This process is repeated until a predetermined film thickness of $SiO_2$ is achieved. Such an ALD process may be significantly slower, providing only a ca. 0.1 nm thickness of silica deposition per cycle. Thus, the pseudo-ALD process may be faster, as it provides 130 times greater deposition per cycle.

Other ALD-like processes are also possible, another ALD-like process may include introduction of $SiCl_4$, but excess $SiCl_4$ may or may not be entirely removed by pumping before water is introduced. In turn, excess water may or may not be entirely removed before $SiCl_4$ is introduced. By not entirely removing excess reagent, as would be appropriate for a true ALD process, faster deposition of $SiO_2$ may be possible. This same strategy of incomplete removal of material could be contemplated for other ALD chemistries that could be used to infiltrate CNTs 106. It is also noted that perfect conformal coating of uniform thickness of CNTs 106 may not always be desirable. An infiltration process may be designed to produce a rough non-uniform thickness coating so as to increase the surface area of the support.

FIG. 10D is a cross-sectional view of the TLC plate intermediate structure shown in FIG. 10C in which primed CNTs 106 have been infiltrated with infiltrant so that a coating material deposits onto priming layer 116 on CNTs 106 to form coating 108 that at least partially coats and extends about a periphery of respective CNTs 106. In the case in which the infiltrant is a silicon precursor gas such as silane, coating 108 may be silicon. However, as discussed above, other precursor gases may be used so that coating 108 may be formed from aluminum or zirconium, or oxides thereof (e.g., use of TMA/TTBS results in a coating of silicon dioxide). Depending on the infiltrant selected, coating 108 may at least partially or substantially coat the entire array of primed CNTs 106 only, or it may also coat the intervening portions of backing layer 102 and catalyst layer 104 between the CNTs 106, resulting in a TLC plate that is one coherent mass.

Coating 108 on respective primed CNTs 106 shown in FIG. 10D forms respective high aspect ratio structures exhibiting an elongated annular geometry (e.g., a substantially hollow cylinder). Primed CNTs 106 act as templates around which the coating material deposits. In some embodiments, coating 108 may be porous or non-porous. The particular aspect ratio of the elongated structures made from coating 108 depends on the height of the template CNTs 106, the deposition time, the process temperature (e.g., temperature of infiltrant and of CNTs 106), or combinations of the foregoing process parameters. FIG. 10DD is a close-up cross-sectional view of a single coated CNT 106 of FIG. 10D. The relative thicknesses of priming layers 114 and 116 is shown in close up FIGS. 10CC and 10DD in order to more clearly show these features.

An average aspect ratio (i.e., ratio of average length to average diameter) of the plurality of elongated structures defined by coating 108 coating respective CNTs 106 may be about 10,000 to about 2,000,000, such about 10,000 to about 1,000,000, or about 100,000 to about 750,000. The average radial thickness of coating 108 coating the CNTs 106 may be about 10 nm to about 250 nm, more particularly about 20 nm to about 150 nm, and even more particularly about 50 nm to about 125 nm (e.g., about 115 to 120 nm). The average length of the elongated structures defined by coating 108 may be substantially the same or similar as the template CNTs 106.

Figure 16:
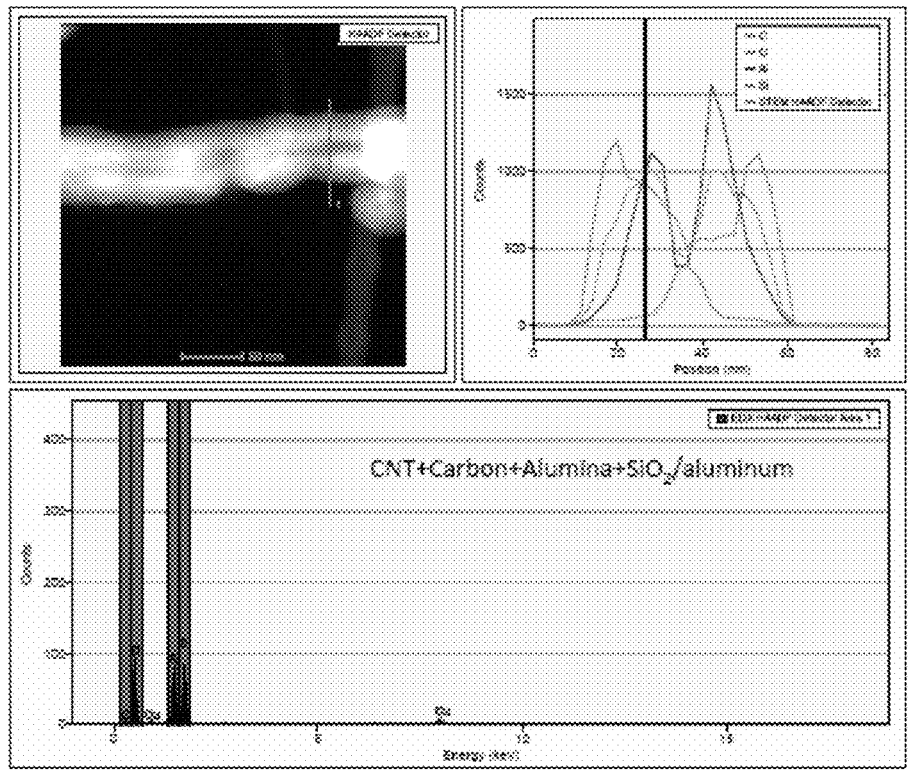
FIG. 16 is a scanning transmission electron microscopy ("STEM") image of an assembly according to an embodiment of the invention including a CNT core primed with an amorphous carbon adhesion priming layer, an alumina adhesion priming layer, and coated with a silica stationary phase.
Figure 19:
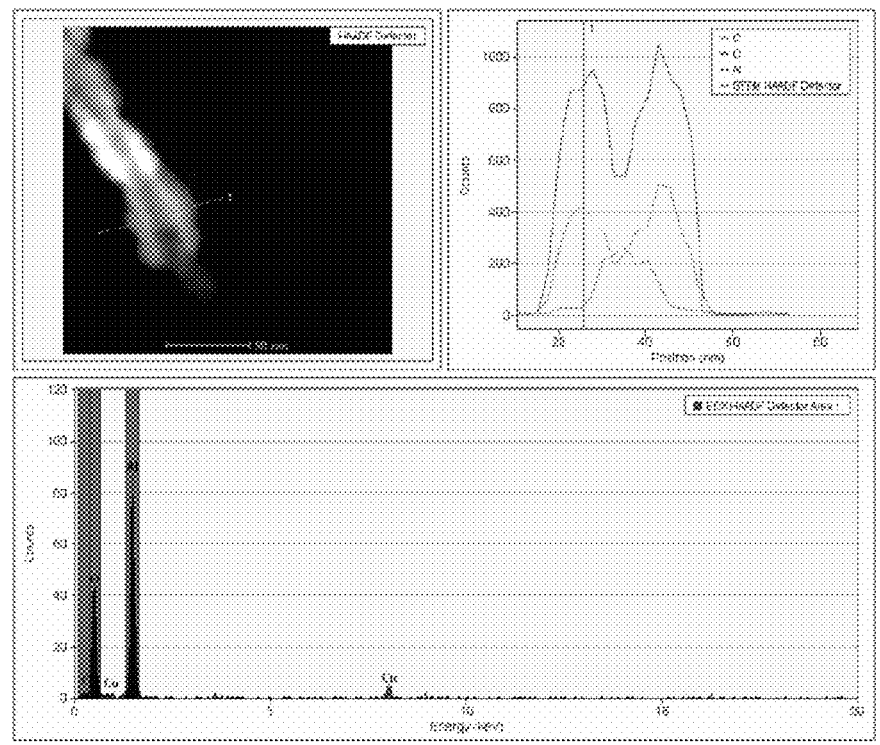
FIG. 19 is a STEM image of an assembly intermediate according to an embodiment of the invention including a CNT core primed with an amorphous carbon adhesion priming layer, and an alumina adhesion priming layer.

FIG. 16 shows an STEM image of a CNT primed with a 4 nm layer of priming carbon, a 10.5 nm layer of priming alumina after being coated with silicon dioxide to form a silicon dioxide shell. The analysis results indicated the expected presence of carbon, aluminum, oxygen, and silicon, with carbon at the center of the assembly, followed by aluminum, and then silicon. FIG. 19 is a STEM image of the assembly intermediate prior to coating with the silica, so that the assembly includes a CNT core primed with an amorphous carbon adhesion priming layer, and an alumina adhesion priming layer. No silica is yet present.

In some cases, random growth of CNTs 106 followed by infiltration and optionally oxidation of coating 108 can pose a potential problem. During the oxidation process of converting silicon to silicon dioxide, the material undergoes a volume expansion due to the addition of the oxygen. The volume expansion may cause the material to delaminate from the backing, particularly during longer, more complete oxidation times and at relatively higher oxidation temperatures. Even if delamination does not appear to have occurred initially, the material may easily buckle and flake away as a result of a slight bump or touch because of the expansion. One way to reduce, minimize, or eliminate such delamination, flaking, or buckling of the material from the backing is by patterning (e.g., zigzag or other non-linear) the CNT growth catalyst, which places voids into the overall structure allowing for volume expansion during the oxidation step. In addition, patterning of the stationary phase medium on the micron-scale may improve separation efficiency.

Figure 15A:
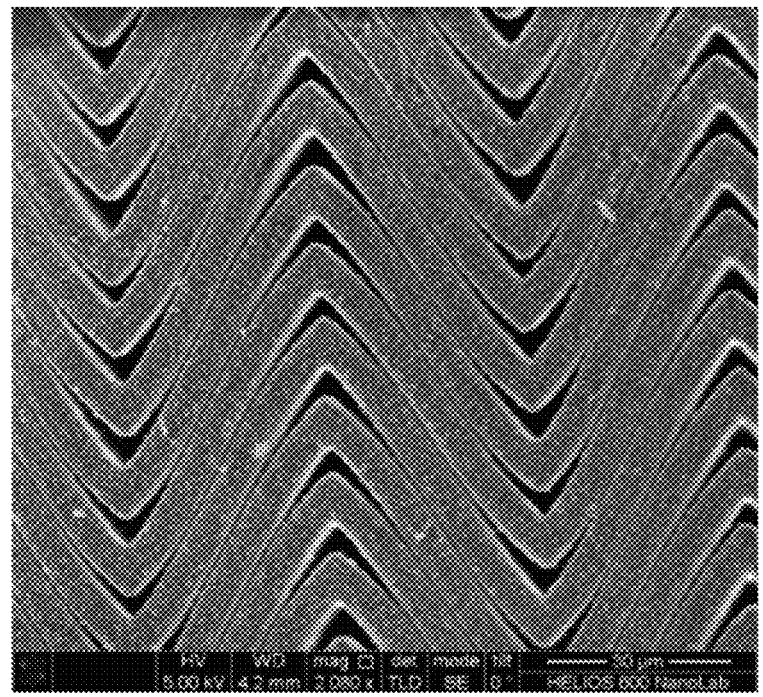
FIG. 15A shows an SEM image of a TLC plate prepared without priming of the CNTs, and in which a silicon precursor of a silica stationary phase is oxidized to silica simultaneously with oxidative removal of the CNTs.
Figure 15B:
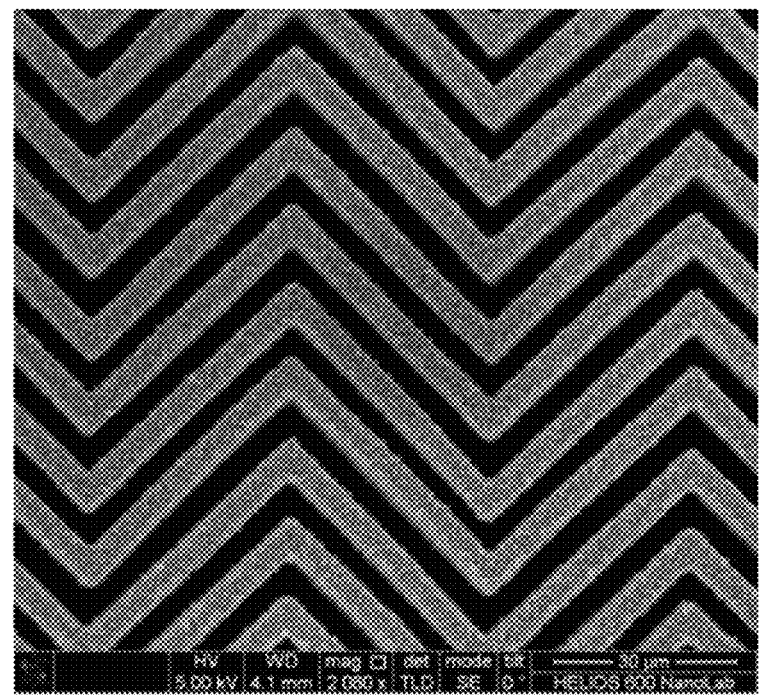
FIG. 15B shows an SEM image of a TLC plate prepared with priming of the CNTs, and in which a silica stationary phase is directly deposited, requiring no oxidation of a stationary phase precursor, followed by oxidative removal of the CNTs at a relatively low temperature.

Another way to aid in reducing, minimizing, or eliminating such distortion is to apply one or more priming adhesion layers to the CNTs prior to infiltration with the stationary phase or precursor thereof. In addition, by infiltrating with silicon dioxide rather than silicon, the oxidation step is not required to oxidize silicon to silicon dioxide, and can be achieved at a lower temperature than where the oxidation step also oxidizes the silicon to silicon dioxide. FIG. 15A illustrates an SEM image of a TLC plate prepared without priming of the CNTs and where the oxidation step oxidizes silicon to silicon dioxide. As readily seen, some distortion is visible where the flow channels between adjacent hedges substantially closes at a mid-section of each hedge (i.e., furthest from where the 90° angle bend of the zig-zag occurs). FIG. 15B illustrates an SEM image of a TLC plate prepared as described herein, including application of a priming amorphous carbon layer and a priming alumina layer. In addition, the primed CNTs were infiltrated with silicon dioxide, so that the oxidation step to remove the CNTs was accomplished at a relatively lower temperature (e.g., about 600° C. as compared to 850° C. to 900° C.)

The selected zigzag pattern may include any of various angles of greater than 0° and less than 180° between the particular portions of the zigzag. For example, the zigzag patterns shown in FIGS. 1, 2, 11A, 11B, 12, 15A, and 15B may include an angle of about 90° between adjacent portions of the zig and zag of the pattern.

As described above, an average bed spacing between adjacent portions of patterned catalyst layer 104 may be from about 0.25 µm to about 50 µm, more particularly from about 2 µm to about 20 µm, and most particularly from about 5 µm to about 15 µm (e.g., about 10 µm). This spacing could be described as distance center to center from one "hedge" to another. The "hedge" width may be from about 0.25 µm to about 15 µm, from about 3 µm to about 10 µm, or from about 4 µm to about 8 µm. The growth of CNTs 106 followed by infiltration with infiltrant and/or growth of coating 108 around CNTs 106 results in less spacing between adjacent elongated structures defined by coating 108 as they grow laterally outward and towards one another. For example, an average spacing between adjacent elongated structures (i.e., "flow channel" width) defined by coating 108 may be between about 0.5 µm and about 30 µm, more particularly between about 2 µm and about 10 µm, and most particularly between about 4 µm and about 8 µm. Such spacing results in a bulk structure having very high bulk porosity i.e., the spacing between adjacent structures act as pores through which the mobile phase and sample carried therewith advance as a result of capillary action. In one embodiment, the flow channel width may be greater than the hedge width (e.g., 5 µm versus 4 µm). When present, porosity of any individual coating 108 (i.e., as opposed to bulk porosity resulting from spacing between adjacent structures) may also contribute to the overall porosity TLC plate.

In an embodiment, CNTs 106 may be partially or substantially completely removed once the coating 108 has been deposited onto CNTs 106. For example, the TLC plate intermediate structure shown in FIG. 10D may be placed into a furnace and heated in the presence of an oxidizing atmosphere (e.g., an oxygen atmosphere) so as to remove (e.g., burn off) substantially all of CNTs 106, leaving only coating 108 disposed on the backing layer 102 and catalyst layer 104 of TLC plate substrate 101. In some embodiments, the stationary phase coating 108 does not require further oxidation prior to use (e.g., it is deposited as silica rather than silicon).

In other embodiments, such an oxidation step may also serve to convert coating 108 into the stationary phase by oxidizing the as-deposited coating 108 if it is not already a chromatography capable stationary phase. For example, if coating 108 is silicon, aluminum, or zirconium, it may be oxidized to silicon oxide, aluminum oxide, or zirconium oxide, respectively. An embodiment of a method for removal of the CNTs 106 may include oxidizing coating 108 using an oxygen plasma. Other methods for at least partially removing CNTs 106 may include dissolution of CNTs 106, or removal by any method.

Where the oxidation step also oxidizes the as deposited coating 108 into an oxide stationary phase, the temperature may need to be higher than where the oxidation step is not required to oxidize the deposited coating. For example, where the coating is oxidized during the oxidation step, the temperature may be from about 800° C. to about 900° C. (e.g., about 850° C. to 900° C.). Where the oxidation step is not required to oxidize the coating 108 (e.g., because coating 108 was already deposited as a desired oxide such as silicon dioxide), the temperature may be substantially lower (e.g., not more than about 750° C., not more than about 700° C., not more than about 650°, not more than about 600° C., or from about 500° C. to about 650° C., or about 600° C.). Methods that deposit coating 108 as an oxide rather than a precursor to an oxide stationary phase may be beneficial, as the lower processing temperature may further increase the mechanical stability of the resulting stationary phase of a TLC plate. In other words, because of the lower temperature and the fact that no oxidizing of the coating 108 occurs during the oxidation step, less distortion of the zig-zag or other pattern occurs (as shown by comparing FIGS. 15A-15B), providing increased mechanical stability and durability.

Figure 10E:
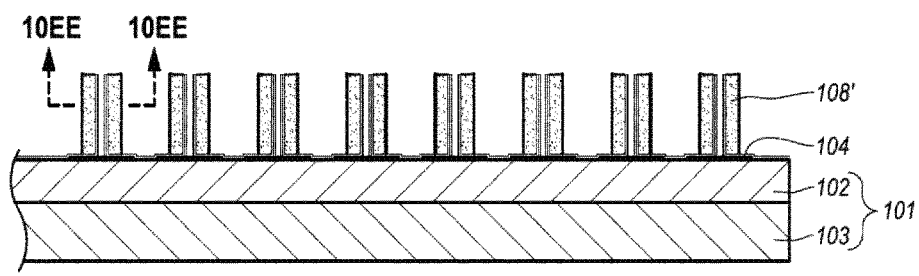
FIG. 10E is a cross-sectional view of the TLC plate intermediate structure of FIG. 10D once the CNTs have been burned off, leaving behind any non-carbon priming layer(s) and the stationary phase structures.
Figure 10E:
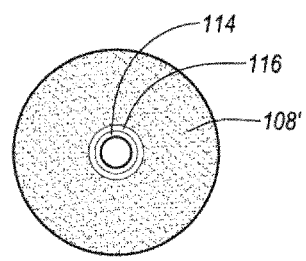

FIG. 10E is a cross-sectional view of the structure shown in FIG. 10D in which the CNTs 106 have been removed. FIG. 10EE is a close up cross-sectional view of stationary phase structures 108' once CNTs 106 have been burned off. FIG. 10E clearly shows the overall high aspect ratio configuration of the stationary phase structures 108'. The dimensions of the plurality of elongated stationary phase structures 108' may be substantially the same or similar dimensions as the plurality of elongated structures defined by coating 108 prior to oxidation of CNTs 106. The oxidation process may occur for at least about 5 hours, more particularly at least about 10 hours, and most particularly for at least about 24 hours. Somewhat reduced processing times may be provided where oxidation of the coating 108 is not required (e.g., about 24 hours is typically sufficient).

As shown in FIGS. 10E and 10EE, in embodiments in which the coating 108 is deposited by ALD or an ALD-like process (e.g., ALD deposition of silicon oxide), the resultant elongated stationary phase structures may be hollow elongated cylinders, with the hollow being where a CNT 106 was located. Where the oxidation step also oxidizes coating 108, depending on the extent of the oxidation process, the elongated stationary phase structures 108' may be substantially solid nanowires in which the space previously occupied by the CNTs 106 is consumed or filled by the oxide.

Removal of CNTs 106 before use of the TLC plate may prevent CNTs 106 from interfering (e.g., through a secondary interaction) with separation of an analyte mixture during use of the TLC plate. In addition, it results in a white and/or transparent stationary phase; thereby making evaluation of the chromatography results easier than if the stationary phase is black or brown. In embodiments in which the coating 108 comprises amorphous carbon, the CNTs 106 may not be removed, as both the coating 108 and CNTs 106 comprise carbon, thereby substantially eliminating the possibility of a secondary interaction as a result of the CNTs 106 being present in the stationary phase formed during infiltration.

In a similar manner, it can be desirable, in some embodiments, that the coating 108' substantially fully coats and covers the adhesion priming layer(s). Any amorphous carbon priming layer may simply be burned away with the CNTs, while an alumina priming layer remains after the oxidation step. Because exteriorly exposed alumina may interfere with the separation results achieved by the TLC plate, the coating 108' may substantially fully coat and cover any alumina adhesion priming layer, so that it is not exposed. For this reason and the fact that the pseudo-ALD deposition of silica may involve the use of an aluminum compound (e.g., TMA), it may be beneficial to further hydrate the stationary phase surface with silanol groups and to apply an amino silane or other silane to coat any exposed aluminum sites, as will be discussed in further detail below.

In some embodiments, the stationary phase structures 108' comprise a material that is white, off white, transparent, or generally light in color so that the compounds of the mobile phase separated during use of the TLC plate are visible on the surface of the TLC plate after being developed. Silicon and/or silicon dioxide are examples of materials that provide such a color contrast. In some embodiments, a fluorescent material (e.g., ZnS) may be incorporated in the TLC plate to produce a fluorescently active TLC plate. This may be accomplished by depositing a thin film on top of or a few monolayers beneath the chromatographic support. This may be done either in the liquid or gas phase. ALD, along with other CVD or liquid phase processes, can be used to place inorganic species into or onto the chromatographic support. For example, the fluorescent material may at least partially coat and/or may be incorporated in the stationary phase structures 108', may at least partially coat intervening portions of backing layer 102 between the stationary phase structures 108', or both. In an embodiment, the fluorescent material may be provided by depositing nanoparticles of a fluorescent inorganic material from a solution or slurry.

After oxidation and removal of CNTs 106, in some embodiments, the TLC plate may be exposed to at least one acid (e.g., HF) or base (e.g., $NH_4OH$) to hydrate the stationary phase structures 108'. For example, the TLC plate so formed may be placed in a furnace in the presence of HCl or other acid (or base) so that HCl (or other) vapors result in placement of hydroxyl or silanol groups onto the surface of stationary phase structures 108' to functionalize stationary phase structures 108'. Additional chemical functionality and selectivity may be added to the stationary phase structures 108' by, for example, silanolization with alkyl moieties through any suitable gas phase chemistry. When the stationary phase structures 108' comprise silica, the silica may also be functionalized by bonding $C_8$ chains, $C_{18}$ chains, $NH_2$, or combinations thereof to the silica.

For example, the TLC plate may be immersed in an acid solution for a selected time period. In an embodiment, the acid solution may comprise 50:50 vol./vol. concentrated HCl and methanol and the TLC plate may be heated therein to reflux temperatures for several hours (e.g., 4-20 hours). The methanol in the acid solution may aid in surface wetting. Other acids that may be used, such as nitric acid, HBr, HF, acetic acid, formic acid, trifluoroacetic acid, or combinations thereof. Exposure to the HCl vapors or introduction of water vapor or acidified water vapor (including the above mentioned acids, or other suitable acids) into the oxidizing chamber while the material is being cooled or for a predetermined time at an elevated temperature may increase the number of hydroxyl groups on the silica surface of the stationary phase structures 108'. Bases such as $NH_4OH$ may similarly be employed to hydrate the surface.

In an embodiment, the stationary phase may be exposed to water vapor after the oxidation step and during cooling from the oxidation temperature to ambient temperature. Acidified water vapor may be employed to hydroxylate the surface. For example, this may be done by placing the TLC plate above a boiling HCl solution so that the vapors of the solution are allowed to interact with the stationary phase. The boiling solution may include methanol to aid in surface wetting. Other components that may be used include other strong acids (e.g., nitric acid, HBr, HF), organic acids (e.g., acetic acid, formic acid, trifluoroacetic acid) or other suitable chemical that can hydroxylate the surface. In one embodiment, exposure may be about 5 minutes, although shorter or longer times may be employed.

Where a base is used, the stationary phase may be immersed in the base etching solution at room temperature for a period of about 12 to about 24 hours (e.g., about 18 hours). Exemplary bases that may be suitable include ammonium hydroxide, calcium hydroxide, sodium hydroxide, potassium hydroxides, other hydroxide salts, or combinations thereof.

The silanol containing surfaces may be silanized using a wide variety of silanes (e.g., mono-chlorosilanes, di-chlorosilanes, tri-chlorosilanes, or combinations thereof). Examples of suitable silanes include alkyl silanes (e.g., octadecyl trichlorosilane, octadecyldimethylchlorosilane, perfluoro alkyl silanes), amino silanes, phenyl silanes, cyano silanes, biphenyl silanes, or combinations thereof. Such silanes may be monofunctional (e.g., including one Si—Cl group, one Si—$OCH_3$ group, one Si—$OCH_2CH_3$ group, or one Si—OC(O)$CH_3$ group), or silanes bearing more than one surface reactive functional group. Molecules such as octadecyldiisopropylchlorosilane are contemplated, where the isopropyl groups impart added hydrolytic stability to the silica TLC plate.

In one embodiment, the stationary phase may be treated by deposition of a an amino silane (e.g., 3-aminopropyltriethoxysilane ("APTES")) to better cover reactive or acidic sites on the surface of the stationary material. Other silanes such as those identified above may also be employed. Such treatments may result in an improvement in the chromatographic performance of the material.

In an embodiment, the TLC plates may be produced with a concentration zone. This involves having an area that has relatively low retention where compounds may be spotted. This allows for the mobile phase to quickly pull the analyte through this area and then the analytes will slow down when they reach the normal sorbent bed. This can be done by making the pre-concentration area with a low density of the stationary phase structures and/or selectively functionalizing this area with a chemical species that allows for reduced retention of analytes.

In some embodiments, substrate 101 may be scribed or partially cut before or after growth of CNTs 106 and/or coating CNTs 106. By scribing or cutting substrate 101, smaller TLC plates may be fabricated by breaking a larger TLC plate along a scribe/cut line of substrate 101.

Figure 11A:
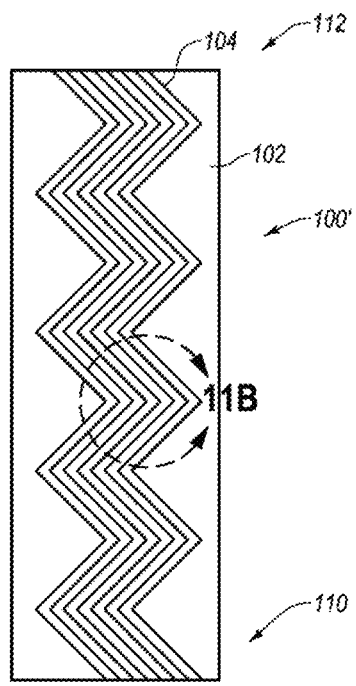
FIG. 11A is a schematic top plan view of a TLC plate manufactured from a TLC plate intermediate structure similar to that of FIG. 1.
Figure 11B:
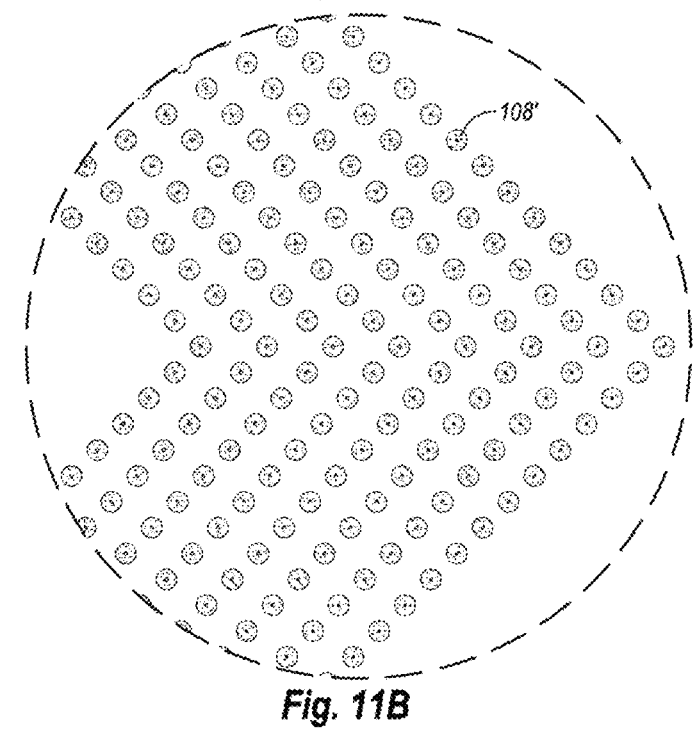
FIG. 11B is a close-up top plan view of the TLC plate intermediate structure of FIG. 11A showing several of the high aspect ratio deposited stationary phase structures disposed on the TLC plate substrate.

FIG. 11A is a top plan view of an embodiment of a TLC plate 100'. FIG. 11B is a close-up view of a portion of TLC plate 100' includes stationary phase structures 108' that are arranged between an end 110 and an end 112 of TLC plate 100'. TLC plates prepared according to the inventive methods disclosed herein provide a stationary phase in which the stationary phase is affixed to the substrate of the TLC plate without the use of any separate binding agent (e.g., calcium sulfate or a polymer). Such binding agents can interfere with the performance of the TLC plate as the result of secondary interactions resulting from the binding agent. The reduction or the elimination of any binding agent may result in a more high efficiency TLC plate, while minimizing and/or preventing such secondary interactions.

Figure 12:
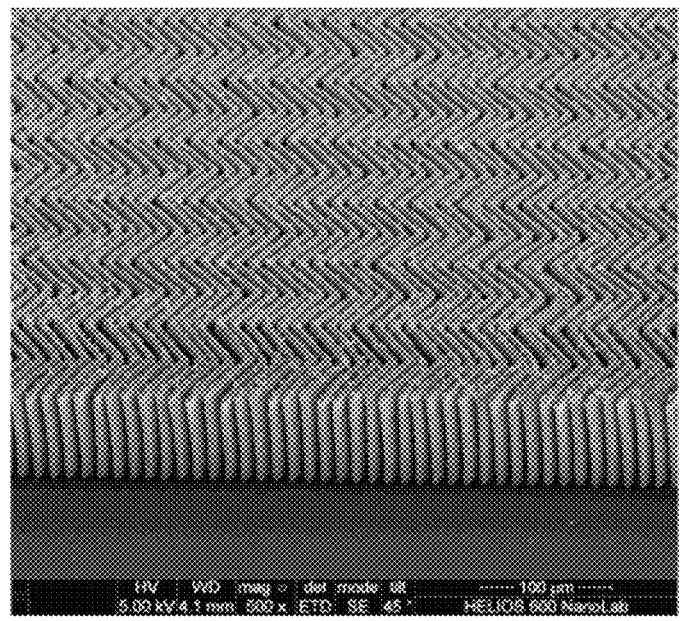
FIG. 12 shows a scanning electron microscopy ("SEM") image of an exemplary non-linear zig-zag stationary phase formed according to the present inventive methods.

The spacing of the stationary phase structures 108' is illustrated in FIGS. 11A and 11B as being generally uniform. However, in some embodiments, the density of the stationary phase structures 108' may be different (e.g., greater or less) in different locations of the TLC plate 100'. For example, the density of the stationary phase structures 108' may be different (e.g., greater or less) near end 110 than near end 112. Additional structures 108' may fill the smaller space between adjacent structure 108' in a given hedge so that each hedge is substantially continuous. Each hedge is separated from an adjacent hedge by a flow channel therebetween (e.g., as shown in FIG. 12). As an alternative to or in addition to the density of the stationary phase structures 108' varying with location, the composition of the stationary phase structures 108' may vary with location. As a non-limiting example, one portion of the stationary phase structures 108' may comprise zirconium oxide and another portion of the stationary phase structures 108' may comprise silica.

Furthermore, TLC plates prepared according to the inventive methods disclosed herein provide a stationary phase having a particularly high porosity. The high porosity, as well as the absence of a binder may result in increased efficiency of the TLC plate during use in analyzing a sample within a mobile phase. In one embodiment, the TLC plates formed according to the disclosed methods are used to analyze a sample material. In one embodiment, the sample to be analyzed is applied to the stationary phase structures 108' of TLC plate 100' (e.g., near end 110). A mobile phase solvent or solvent mixture is then drawn along TLC plate 100' (e.g., upwardly) by capillary action (e.g., by placing TLC plate 100' in a container including the solvent or solvent mixture), or the mobile phase solvent or solvent mixture by be forced through TLC plate 100'. As the solvent or solvent mixture is drawn along the TLC plate 100' via capillary action toward opposite end 112, the sample is dissolved in the mobile phase and separation of components within the sample is achieved because different components of the sample ascend the TLC plate 100' at different rates. The high aspect ratio stationary phase structures 108' as well as the bulk porosity as a result of the spacing between individual high aspect ratio stationary phase structures 108' results in excellent separation efficiency of components within the sample as the sample components are carried through the stationary phase structures 108' by the mobile phase (e.g., a solvent or solvent mixture). The TLC plates 100' may also be used in HPTLC in which one or more of the method of use steps may be automated so as to increase the resolution achieved and to allow more accurate quantization.

III. Working Examples

The following working examples are for illustrative purposes only and are not meant to be limiting with regards to the scope of the specification or the appended claims. Example 1 is representative of how the CNT structures were grown for all examples carried out.

Example 1

The masks for photolithography were all based on a zig-zag geometry with 90° angles. Silicon wafers (University Wafers, South Boston, Mass.), 4" diameter, were used as the backing material. A thin film of photoresist, AZ-3312-F (AZ Electronic Materials USA Corp, Somerville, N.J.), was spin coated onto the wafer. The resulting wafer was patterned via photolithography (Karl Suss Mask Aligner, Vt., USA), followed by e-beam evaporation (Benton Vacuum E-beam Evaporator, Moorestown, N.J.) of a thin barrier layer of alumina (35 nm), and thermal evaporation (custom-built apparatus) of a few nanometers of iron (6 nm). The iron deposition was monitored using a quartz crystal device. The photoresist was then lifted off with a resist stripper (Micropsoit 1165, MicroChem, Newton, Mass.), leaving a pattern of $Al_2O_3$/Fe at the surface.

The photolithographically patterned wafer was loaded into a fused silica tube (22 mm ID), preheated at 200° C. in a Lindberg/Blue M tube furnace (Thermo Electron Corporation, Marietta, Ohio), and then heated to 400° C. under flow of argon. The temperature was then raised from 400° C. to 750° C. in an atmosphere of hydrogen (400 sccm) to reduce iron to its elemental form and simultaneously produce iron nanoparticles. CNTs were grown for 2 minutes at 750° C. to a height of about 50 μm with ethylene (Grade 5.0, 99.999% from Air Gas) at 1000 sccm and hydrogen (Air Gas), at 400 sccm. The material was cooled under an atmosphere of argon to 200° C.

Comparative Example 2

FIG. 13A shows an SEM image for a silica coating configuration of grown CNTs. As shown in FIG. 13A, the resulting thin $SiO_2$ films applied without a priming layer lacked conformality and often showed a large number of pearl-like features. This lack of conformal growth may be expected to negatively affect a TLC plate's mechanical stability. To test mechanical stability, after removal of the CNTs via air oxidation, the TLC plate was submerged in water and immediate failure/delamination was observed. The pearl-like growth observed structure corresponding to FIG. 13A was thought to be the result of an insufficient number of nucleation sites on the CNTs, which are quite chemically inert.

Examples 3-6

The use of one or more adhesion promoters (FIGS. 13B-13D), such as the contemplated amorphous carbon and/or alumina priming layers discussed in more detail below was believed to increase the number of nucleation sites on the CNTs, thereby allowing more conformal growth to take place. It was thought that only a very thin layer, perhaps only a few nanometers, of one or more adhesion priming layers may be sufficient to increase the number of nucleation sites available for subsequent infiltration or coating (e.g., through ALD or similar process). Accordingly, a small amount of carbon was deposited onto CNTs using ethylene diluted in argon at 900° C. The resulting carbon layers showed good conformality and even some measure crystallinity, as suggested by the texture of the TEM images of FIGS. 14A and 14B.

To explore whether these few nanometers of carbon might improve ALD or pseudo-ALD on CNTs, and to show that these plates indeed exhibit the desired stability and chromatographic properties, four types of depositions were performed on patterned CNT forests using different combinations of carbon (C), true ALD of $Al_2O_3$, and deposition of pseudo-$SiO_2$: (i) Example 3—CNT—pseudo-$SiO_2$(8), (ii) Example 4—CNT-C(4 nm)—pseudo-$SiO_2$(8), (iii) Example 5—CNT-$Al_2O_3$(7 nm)—pseudo-$SiO_2$(8), and (iv) Example 6—CNT-C(4 nm)-$Al_2O_3$(7 nm)—pseudo-$SiO_2$(8), where the number in parentheses refers to the number of pseudo ALD cycles, one cycle referring to the introduction of both precursors for the process.

Each series of depositions was then performed three times, from start to finish, in separate fabrications. They were then oxidized to remove both the CNT framework and the carbon adhesion priming layer. It was not necessary to convert Si to $SiO_2$, so the nanotubes and carbon layer could be burned out at a relatively low temperature (about 600° C.). Finally, the plates were visually inspected for whiteness (the more white the plate the greater the degree of deposition, as it hid the darker substrate), and immersed in water. As expected, the CNT-pseudo-$SiO_2$(8) plates visually showed the least amount of $SiO_2$ deposition and all of them failed the water immersion test, showing immediate delamination/removal of the layer. The CNT-C(4 nm)-pseudo-$SiO_2$(8) plates showed more $SiO_2$ deposition, but about 50% of them (FIG. 13B) failed the water immersion test. The CNT-$Al_2O_3$(7 nm)-pseudo-$SiO_2$(8) plates of FIG. 13C performed about as well as the CNT-carbon(4 nm)-pseudo-$SiO_2$(8) plates, with one plate completely passing and about half of another plate passing the immersion test. The best performing substrates (FIG. 13D) included both carbon and $Al_2O_3$ adhesion priming layers.

Structures of FIG. 13D showed the greatest deposition of inorganic material (greatest whiteness) and 2.5 of 3 plates passed the immersion test (only part of one plate failed). FIGS. 15A and 15B show SEM micrographs of portions of TLC plates prepared without any priming layers, and with oxidation of a silicon infiltrant to silica (FIG. 15A), showing some distortion of the features. FIG. 15B shows a portion of a TLC plate made with carbon and alumina adhesion priming layers and with deposition of silica directly, so that no oxidation of the deposited stationary phase is required. The structure of FIG. 15B shows straight, undistorted features.

Example 7

More stable materials, which better withstood the water immersion test, were found to be possible by increasing the number of $Al_2O_3$ adhesion priming layers from 70 cycles to 105 cycles (i.e., a thickness of 10.5 nm rather than 7 nm). TEM/STEM analysis of the resulting CNT-C(4 nm)-$Al_2O_3$ (10.5 nm)-pseudo-$SiO_2$(8) materials showed the expected sequential encapsulation of the CNTs and carbon with $Al_2O_3$ and pseudo-$SiO_2$ (see FIGS. 16 and 19).

TLC was then performed on the (CNT-C(4 nm)-$Al_2O_3$ (10.5 nm)-pseudo-$SiO_2$(8)) plates after hydrating the plates by immersion in a pH 10 solution of $NH_4OH$ for 18 hours, and rinsing with water to neutrality.

TLC was performed using the silica plates that were prepared including 4 nm and 10.5 nm adhesion priming layers of amorphous carbon and alumina respectively, followed by pseudo-ALD of silica. The silica plates were further hydrated before chromatography by immersion in a pH 10 $NH_4OH$ solution for 18 hours followed by rinsing with water to neutrality. This was done to repopulate the silica surface with silanol (SiOH) groups because the silica had been heated to a temperature of over 200° C. TLC of a CAMAG test dye mixture was then performed under normal phase conditions with the recommended mobile phase (toluene). The run times for the plates were short: about 30 seconds development times for 30 mm development distances. In addition, all of the analytes in the test mixture generally showed substantial streaking except the fastest moving analyte, which appeared as a tight band (in two instances with plate counts of about 77,000 N m$^{-1}$ and about 100,000 N m$^{-1}$) at a moderate retention factor ($R_f$) value of about 0.6. These results suggested the presence of strongly adsorbing sites that interact to a greater extent with the more polar (more strongly retained) analytes in the test mixture. The TLC plates of this test are shown in FIGS. 20A and 20B.

Example 8

Metal impurities, including aluminum, can create strongly adsorbing sites in silica that deleteriously affect chromatography. While in theory the plates as prepared should be entirely covered by silica, it was thought that one possible source of strongly adsorbing sites could be aluminum from the pseudo-ALD deposition of $SiO_2$, i.e., alumina from $Al(CH_3)_3$ is deposited as a catalyst at the start of each AB deposition cycle.

X-ray photoelectron spectroscopy (XPS) was performed on a CNT-amorphous C(4 nm)-$Al_2O_3$(7 nm)-pseudo-$SiO_2$ (8 cycles) plate to determine whether any aluminum was present in the upper approximately 5 nm-10 nm of the $SiO_2$ film. A negative signal (no Al by XPS) would indicate that the aluminum was entirely covered with a thick layer of silica. A small positive signal would be ambiguous—the Al might be covered with a moderately thick film of $SiO_2$ or it might be near enough to the surface to create highly acidic/adsorptive sites. XPS showed about 2 atomic percent Al on the TLC material. Interestingly, significantly less Al (0.2 atomic percent) was found on a planar pseudo-$SiO_2$ film, which suggested that the deposition of pseudo-$SiO_2$ on the curved nanotubes may not be quite the same as on a planar substrate.

In addition to XPS, diffuse reflectance infrared Fourier transform spectroscopy ("DRIFTS") was performed on the materials and compared with a commercially available silica material produced for HPLC. Highly adsorptive silicas with highly acidic/isolated silanols that show poor chromatographic performance have peak maxima for silanols at or greater than 3740 cm$^{-1}$, while silicas that show better chromatographic performance show a maximum below this value, which corresponds to associated/more closely spaced/hydrogen bonded silanols. The DRIFT analysis of our material gave a silanol peak position of 3740.5 cm$^{-1}$, suggesting the presence of at least some highly adsorptive sites, while the commercial silica standard gave a value of 3739.9 cm$^{-1}$.

Thus, chromatographic, XPS, and DRIFT analyses suggested that strongly adsorbing sites might be present in the stationary phase/support and that these strongly adsorptive sites may be due to aluminum. To further probe this issue, a small amount (0.1%) of triethylamine (TEA) was added to the mobile phase. TEA interacts strongly with isolated silanols/ strongly adsorbing sites. TEA had two effects on TLC separations. First, it changed the chromatographic characteristics of the mobile phase, by strengthening it, which resulted in higher $R_f$ values for the analytes. In fact, the analytes largely ran together with $R_f$ values of about 0.8. The addition of TEA eliminated streaking on the plates. The results from these three experiments are consistent with the presence of strongly adsorbing sites on the TLC plates.

Because of this, it may be advantageous to further treat the silica stationary phase with a material that will bind to or otherwise cover up any strongly adsorbing sites on the TLC plates. For this purpose, the silica is treated with a silane, such as an amino silane (e.g., 3-aminopropyltriethoxysilane (APTES)). The thickness of the APTES coating on the $SiO_2$ features of the TLC plates was monitored by spectroscopic ellipsometry via witness shards of planar silicon wafers (APTES thickness: 1.6±0.1 nm). The advancing and receding water contact angles on these planar surfaces were 46.3±1.7° and 8.4±1.0°. XPS also confirmed APTES deposition, showing a small but noticeable nitrogen signal (N1s:Si2p ratio of 2:25) for the APTES-coated TLC plate.

Figure 17:
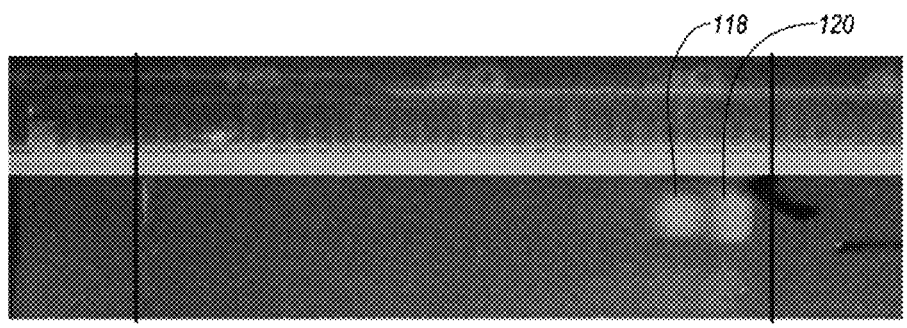
FIG. 17 shows the separation results of two fluorescent dyes on a TLC plate according to an embodiment of the invention.
Figure 18:
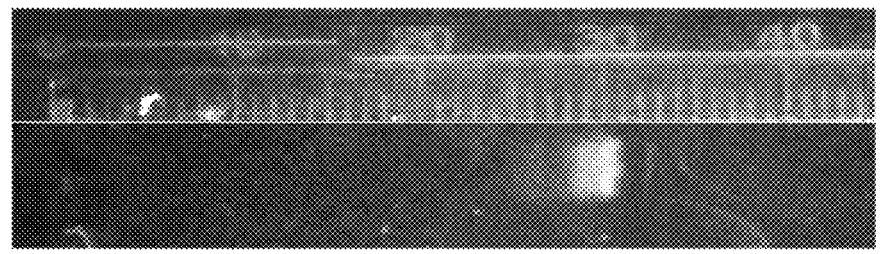
FIG. 18 shows the separation results of four fluorescent dyes on a TLC plate according to an embodiment of the invention.

FIGS. 17 and 18 show performance characteristics of TLC plates that also include such an amino silane coating. FIG. 17 shows separation of two fluorescent dyes, Eosin Y disodium and sulforhodamine B over a 30 mm run distance using 1:100 LiCl:Methanol mobile phase. Analyte concentration in the lower track was about 10% of the concentration of analytes in the upper track. The TLC plate shown in FIG. 17 included 3 μm wide hedges and 5.66 μm flow channels (e.g., in a zig-zag pattern similar to that seen in FIG. 12). Development occurred in 1:08 minutes. This same separation was performed on a commercially available amino-HPTLC plate under the same conditions. Comparing the solvent front migration times between the two TLC plates (microfabricated vs. HPTLC) the TLC plate of FIG. 17 ran about 3 times faster (amino-HPTLC development time 3:26 min).

The green spot on the TLC plate shown in FIG. 17 (labeled 118), which is probably most representative of the separation, showed an $R_f$ value of 0.85 with 93,000 plates per meter (N $m^{-1}$). The orange spot (labeled 120), which migrated further and with an $R_f$ of 0.94, may have been focused by the solvent front so the corresponding value of N $m^{-1}$ (158,000 N $m^{-1}$) may be inflated. This two component separation was reproduced on three separate TLC plates. It was apparent that surface functionalization with APTES rendered a material that was more suitable for chromatography.

FIG. 18 shows a TLC plate similar to that of FIG. 17, but which was used to separate four fluorescent dyes (Eosin Y disodium salt, sulforhodamine B, rhodamine 6G, and fluorescein sodium salt) using a 1:70:30 LiCl:methanol:isopropanol mobile phase. Development occurred in 1:52 minutes over a 30 mm distance (same distance as FIG. 17). This separation showed improved efficiencies over the previous separations, which may be attributed to a reduction in the mobile phase migration rate due to a more viscous mobile phase, and which may have allowed the separation to occur at a more optimal mobile phase velocity. The efficiencies obtained in this separation ranged from 125,000 to 225,000 N $m^{-1}$ (more specifically, 125000, 225000, 175000, and 225000 N $m^{-1}$ at $R_f$ values of 0.79, 0.86, 0.89, and 0.94, respectively). The separated dyes appeared as symmetrical bands, which would again be consistent with APTES covering highly adsoptive sites on the pseudo-ALD deposited $SiO_2$. Comparing these results to a commercial available amino-phase HPTLC plate showed that our TLC plates were about 6 times more efficient and about 4 times faster. Thus, microfabricated TLC plates allow for both extremely efficient separations along with an increase in speed of anaylsis. The fluorescent images were captured under 254 nm light.

The use of one or more priming layers, the use of ALD type reactions to coat the primed CNTs with silica, and further treatment with an amino silane provides much higher efficiencies than previous work done by the present inventors. For example, the maximum number of theoretical plates per meter (N $m^{-1}$) previously obtained was about 75,000 N $m^{-1}$. The process described above produced a chromatographic medium that gave a maximum of 225,000 N $m^{-1}$.

Example 9

Example 9 included both amorphous carbon and alumina adhesion priming of the CNTs, included coating silica directly onto the primed CNTs without the need to oxidize a deposited stationary phase precursor, and which also included treatment with an amino silane to increase the separation efficiency of the resulting TLC plate. In these respects, Example 9 is similar to Example 8.

The masks for photolithography were all based on a zigzag geometry with about 90° angles. In each case the hedges and flow channels were 100 μm long between bends. One configuration included a 3 μm hedge width with a 5.66 μm flow channel. Another configuration included a 4 μm hedge with a 5 μm flow channel.

Silicon wafers (University Wafers, South Boston, Mass.), 4" diameter, were used as the backing material. A thin film of photoresist, AZ-3312-F (AZ Electronic Materials USA Corp, Somerville, N.J.), was spin coated onto the wafer. The resulting wafer was patterned via photolithography (Karl Suss Mask Aligner, Vt., USA), followed by e-beam evaporation (Benton Vacuum E-beam Evaporator, Moorestown, N.J.) of a thin barrier layer of alumina (35 nm), and thermal evaporation (custom-built apparatus) of a few nanometers of iron (6 nm). The iron deposition was monitored using a quartz crystal device. The photoresist was then lifted off with a resist stripper (Microposit 1165, MicroChem, Newton, Mass.), leaving a pattern of $Al_2O_3$/Fe at the surface.

The photolithographically patterned wafer was loaded into a fused silica tube (22 mm ID), preheated at 200° C. in a Lindberg/Blue M tube furnace (Thermo Electron Corporation, Marietta, Ohio), and then heated to 400° C. under flow of argon. The temperature was then raised from 400° C. to 750° C. in an atmosphere of hydrogen (400 sccm) to reduce iron to its elemental form and simultaneously produce iron nanoparticles. CNTs were grown for 2 minutes at 750° C. to a height of about 50 μm with ethylene (Grade 5.0, 99.999% from Air Gas) at 1000 sccm and hydrogen (Air Gas), at 400 sccm. The material was cooled under an atmosphere of argon to 200° C.

To improve adhesion and better facilitate deposition of the later applied stationary phase, a thin layer (4 nm) of amorphous carbon was deposited onto the CNTs. The CNTs were placed in the same tube furnace used for CNT growth and the temperature was raised to 900° C. under an argon atmosphere. Amorphous carbon was then deposited at 900° C. from ethylene (150 sccm) and argon (300 sccm) for 45 s (deposition rate was about 5 nm $min^{-1}$). Afterwards, the material was cooled to 200° C. under argon. The thickness of the amorphous carbon adhesion priming layer was determined on planar (100) silicon substrates via spectroscopic ellipsometry (M-2000D, J.A. Woollam Co., Inc., Lincoln, Nebr.). In addition to determining the deposition rate, the deposition profile of the furnace was measured to ensure that carbon was deposited in a uniform manner over a uniform area (see FIG. 21).

ALD of a second adhesion priming layer comprising $Al_2O_3$ was performed using a Cambridge Fiji F200 system (Cambridge NanoTech Inc., Cambridge, Mass.). Trimethylaluminum (97%, Sigma-Aldrich) and water were cycled in a serial, repeating (e.g., in an ABAB fashion) fashion. The deposition was performed at 250° C. In one configuration, 70 AB cycles were performed to produce an $Al_2O_3$ film thickness of 7 nm. In another configuration, 105 AB cycles were performed to produce a film thickness of 10.5 nm. Film thicknesses were monitored via ellipsometry (M-2000D, J.A. Woollam Co., Inc., Lincoln, Nebr.), with film growth of about 0.1 nm cycle$^{-1}$.

Pseudo-ALD of SiO$_2$ was also performed with a Cambridge Fiji F200 system using trimethylaluminum (97%, Sigma-Aldrich) and TTBS (99.999%, Sigma-Aldrich), which were cycled in an ABAB type fashion. The deposition was performed at 235° C. at a rate of about 13 nm cycle$^{-1}$. 8 cycles were performed to produce the SiO$_2$ film. Film thicknesses were again monitored via spectroscopic ellipsometry (M-2000D, J.A. Woollam Co., Inc., Lincoln, Nebr.).

To produce a white material for chromatography the CNTs were removed via air oxidation. The silica coated CNTs were placed into a preheated (200° C.) bench top furnace (Thermolyne 6000 Furnace, Dubuque, Iowa) and heated to 600° C. at 1° C. min$^{-1}$. The material was held at 600° C. for 17.33 hrs., for a total processing time of 24 hrs. The furnace was then cooled to 200° C.

Because the SiO$_2$ material was subjected to temperatures above 200° C., it was further subjected to a silanol treatment to increase the number of hydroxyl or silanol groups. Surface silanol repopulation was performed with a pH 10 NH$_4$OH etching solution at room temperature for 18 hours. After 18 hours the material was removed from solution and rinsed with deionized water to neutrality. The material was dried at 120° C. prior to chromatography or APTES deposition.

TLC plates were placed into a freshly prepared solution of 1% APTES (≥98%, Sigma-Aldrich) in water-saturated toluene (≥99.8%, Sigma-Aldrich) and heated to 70° C. The solution was held at this temperature for 10 min after which the TLC plate was removed and rinsed three times with methanol (≥99%, Sigma-Aldrich). The amino silane film thickness was measured on a model planar silicon surface via spectroscopic ellipsometry.

X-ray photoelectron spectroscopy (XPS) was performed with a Surface Science SSX-100 X-ray photoelectron spectrometer (serviced by Service Physics, Bend, OR) with a monochromatic Al K$_\alpha$ source, a hemispherical analyzer, and a take-off angle of 35°. Survey scans as well as narrow scans were recorded with an 800 μm×800 μm spot size. The XP spectra were analyzed using the ESCA Data Analysis Application (Version: Analysis 25 V.01.02) software. Diffuse reflectance infrared Fourier transform spectroscopy (DRIFTS) was performed using a Thermo Scientific Nicolet 6700 FT-IR. Both the microfabricated material (scraped from microfabricated TLC plates) and commercially available silica (Sepax HP-Silica, 3 μm, 120 Å, Sepax Technologies, Inc., Del.) were scanned 128 times with a resolution of 0.964 cm$^{-1}$. The spectra were analyzed using the instrument OMNIC 8.1.11 software.

Test dye mixture III solution in toluene containing indophenol, ariabel red, Sudan blue II, Sudan IV, and dimethylaminoazobenzene from CAMAG (Muttenz, Switzerland) was diluted in hexanes to produce a 1% v/v solution. A 1 μL or 3 μL volume of this solution was applied as a 3 mm band at the bottom of the TLC plate using a Linomat 5 spotter (CAMAG, Muttenz, Switzerland). The band was applied 5 mm from the bottom of the plate. The plate was then placed in a 10×10 cm twin trough chamber (CAMAG, Muttenz, Switzerland) and pre-equilibrated with the vapors of the mobile phase, toluene (99.8%, Sigma-Aldrich) with or without 0.1% v/v triethylamine (99.5%, Sigma-Aldrich), for 10 min. After the pre-equilibration, 3 mL of the mobile phase was introduced at the bottom of the plate to commence chromatography. The TLC plate was developed over a 30 mm distance.

Eosin Y disodium salt (~85%, Sigma-Aldrich) and sulforhodamine B (75%, Sigma-Aldrich) were dissolved together in methanol to concentrations of about 5×10$^{-7}$ M. 0.5 μL of this solution was applied as a 3 mm band, 5 mm from the bottom of the TLC plate, using the Linomat 5 spotter (CAMAG, Muttenz, Switzerland). The spotted plate was placed in a twin trough chamber and allowed to pre-equilibrate with the vapors of the mobile phase, 1:100 LiCl:methanol (LiCl, >99%, EMD, Gibbstown, N.J.), for 10 minutes. After the pre-equilibration step, 3 mL of the mobile phase was introduced to commence chromatography. The TLC plate was developed over a 30 mm distance. The results are shown in FIG. 17.

Eosin Y disodium salt (~85%, Sigma-Aldrich), sulforhodamine B (75%, Sigma-Aldrich), rhodamine 6G (~95%, Sigma-Aldrich), and fluorescein sodium salt (98%, Sigma-Aldrich) were dissolved in methanol to a concentration of about 5×10$^{-7}$ M. 0.5 μL of this solution was applied as a 3 mm band, 5 mm from the bottom of the TLC plate, using the Linomat 5 spotter (CAMAG, Muttenz, Switzerland). The spotted plate was placed into the twin trough chamber and allowed to pre-equilibrate with the vapors of the mobile phase: 1:70:30 LiCl:methanol:isopropanol (isopropanol, ≥99%, Sigma-Aldrich), for 10 minutes. After this pre-equilibration, 3 mL of the mobile phase was introduced to commence chromatography. The TLC plate was developed over a 30 mm distance. The results are shown in FIG. 18.

Imaging of the separated dyes was performed using a digital camera (Canon PowerShot S95, Canon USA, Inc., Lke Success, N.Y.). The TLC plate was exposed to short wavelength UV light (254 nm) (Model UVG-11 Mineralight Lamp, Ultra-Violet Products, Inc., San Gabriel, Calif.) for fluorescent visualization. All images were processed using ImageJ (ImageJ 1.42q, National Institutes of Health, USA).

Retention factors ($R_f$) were calculated with the following equation:

$$R_f = \frac{Z_s}{Z_f}$$

where $Z_s$ is the analyte migration distance from the application origin and $Z_f$ is the distance the solvent front traveled also from the application origin. Chromatographic efficiencies were determined by the number of theoretical plates (N) according to:

$$N = 16\left(\frac{Z_f R_f}{W}\right)^2$$

where W is the width of the chromatographic band.

All SEM images were captured with an FEI Helios Nanolab 600 (Hillsboro, Oreg.). TEM images were captured using an FEI Tecnai F20 Analytical STEM (Hillsboro, Oreg.). The results achieved with Example 9 were as reported above relative to Example 8. For example, the TLC plates showed an efficiency that was about 6 times greater than commercially available amino-phase HPTLC plates. In addition, the TLC plates were about 4 times faster.

The described embodiments may be used in different types of liquid or gas chromatography, such as high-performance liquid chromatography ("HPLC"), ultra-performance liquid chromatography ("UPLC"), microfluidic applications, pressurized liquid chromatography, microfluidic or nanofluidic chromatography, circular or anti-circular TLC, and any other type of chromatography application. Various columns or separations media for HPLC, UPLC, microfluidic applications containing the patterned or un-patterned infiltrated CNTs, a number of different assays (e.g., fingerprinting of natural products or screening for radical scavengers and anti-oxidants) are within the scope of the present disclosure.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A method for manufacturing a chromatography apparatus, the method comprising:
    forming a catalyst layer on a substrate;
    forming a layer of elongated nanostructures on the catalyst layer;
    priming the elongated nanostructures to form a layer of primed elongated nanostructures by at least partially coating the elongated nanostructures with at least one adhesion priming layer for promoting subsequent deposition of a coating thereon; and
    at least partially coating the primed elongated nanostructures with the coating, wherein the coating includes at least one member selected from the group consisting of aluminum, aluminum oxide, titanium, and titanium oxide.

2. The method as recited in claim 1, further comprising exposing the coating to at least one of an acid or base in order to bond hydroxyl groups to the stationary phase.

3. The method as recited in claim 2, further comprising exposing the stationary phase to a silane in order to bond silane groups to the stationary phase.

4. The method as recited in claim 3, wherein the silane comprises an amino silane.

5. The method as recited in claim 4, wherein the amino silane comprises 3-aminopropyltriethoxysilane.

6. The method as recited in claim 1, further comprising, after the act of at least partially coating the primed elongated nanostructures with the coating, at least partially removing the elongated nanostructures.

7. The method as recited in claim 6, wherein the act of priming the elongated nanostructures includes priming the elongated nanostructures with an adhesion priming layer comprising amorphous carbon having a thickness of not more than about 10 nm.

8. The method as recited in claim 7, wherein the act of at least partially removing the elongated nanostructures also removes the adhesion priming layer comprising the amorphous carbon.

9. The method as recited in claim 6, wherein the act of priming the elongated nanostructures comprises priming the elongated nanostructures with a first adhesion priming layer and a second adhesion priming layer, wherein the first and second adhesion priming layers include different materials.

10. The method as recited in claim 9, wherein the first adhesion priming layer includes amorphous carbon and the second adhesion priming layer comprises alumina.

11. The method as recited in claim 10, wherein the first adhesion priming layer comprising the amorphous carbon has a thickness of not more than about 10 nm.

12. The method as recited in claim 10, wherein the act of at least partially removing the elongated nanostructures also removes the first adhesion priming layer comprising the amorphous carbon.

13. The method as recited in claim 1, wherein forming a layer of elongated nanostructures on the catalyst layer comprises growing a layer of carbon nanotubes on the catalyst layer.

14. The method as recited in claim 1, wherein the at least one material of the coating is selected from the group consisting of aluminum oxide and titanium oxide.

15. The method as recited in claim 14, wherein at least partially coating the primed elongated nanostructures with the coating includes at least partially infiltrating the elongated nanostructures with the at least one material by atomic layer deposition or pseudo-atomic layer deposition.

16. The method as recited in claim 1, wherein the catalyst layer, the elongated nanostructures, and the coating including at least one of a stationary phase or a precursor of a stationary phase form a zigzag pattern.

17. The method as recited in claim 1, wherein the at least one adhesion priming layer comprises at least one material selected from the group consisting of silicon, silicon dioxide, silicon nitride, aluminum, aluminum oxide, titanium, titanium oxide, zirconium, and zirconium oxide.

18. The method as recited in claim 1, wherein the act of priming the elongated nanostructures includes depositing the at least one adhesion priming layer via chemical vapor deposition or via a solution.

19. The method as recited in claim 1, wherein the elongated nanostructures include carbon nanotubes.

20. A method for manufacturing a chromatography apparatus, the method comprising:
    forming a layer of carbon nanotubes;
    priming the carbon nanotubes to form a layer of primed carbon nanotubes by at least partially coating the carbon nanotubes with at least one adhesion priming layer for promoting subsequent deposition of a coating thereon; and
    at least partially coating the primed carbon nanotubes with the coating, wherein the coating includes at least one member selected from the group consisting of aluminum oxide and titanium oxide.

21. The method as recited in claim 20, wherein the at least one material of the coating is aluminum oxide.

22. The method as recited in claim 20, wherein the at least one material of the coating is titanium oxide.

23. A method for manufacturing a chromatography apparatus, the method comprising:
    forming a layer of carbon nanotubes;
    at least partially coating the carbon nanotubes to form a layer of coated carbon nanotubes by at least partially coating the carbon nanotubes with at least one adhesion layer for promoting subsequent deposition of another coating thereon; and
    at least partially coating the coated carbon nanotubes with the another coating, wherein the another coating includes at least one oxide material, selected from the group consisting of aluminum oxide and titanium oxide.

24. The method as recited in claim 23, wherein the at least one oxide material includes titanium oxide.

25. The method as recited in claim 23, wherein the at least one oxide material includes aluminum oxide.

* * * * *